United States Patent [19]

Masuda et al.

[11] Patent Number: 6,075,055
[45] Date of Patent: Jun. 13, 2000

[54] PHENYLALKANE AMIDE DERIVATIVES AND AGRICULTURAL OR HORTICULTURAL FUNGICIDES

[75] Inventors: Katsumi Masuda; Ikumi Urushibata; Tsuyoshi Asahara, all of Iwata-gun; Katsumi Furuse, Ogasa-gun; Yoshiyuki Kojima; Hiroshi Abe, both of Kakegawa, all of Japan

[73] Assignees: Kumiai Chemical Industry Co., Ltd.; Ihara Chemical Industry Co., Ltd., both of Tokyo, Japan

[21] Appl. No.: 08/952,665

[22] PCT Filed: May 29, 1996

[86] PCT No.: PCT/JP96/01419

§ 371 Date: Dec. 1, 1997

§ 102(e) Date: Dec. 1, 1997

[87] PCT Pub. No.: WO96/38406

PCT Pub. Date: Dec. 5, 1996

[30] Foreign Application Priority Data

May 31, 1995 [JP] Japan ..................... 7-157000

[51] Int. Cl.[7] .................. A01N 37/18; C07C 233/00
[52] U.S. Cl. .................. 514/619; 514/538; 514/618; 558/426; 558/544; 560/9; 560/30; 560/39; 560/41; 564/162; 564/164; 564/182
[58] Field of Search .................. 560/30, 9, 39, 560/41; 558/426, 544; 564/162, 164, 182; 514/538, 618, 619

[56] References Cited

U.S. PATENT DOCUMENTS 5,508,436  4/1996  Fisher et al. ..................... 548/544

FOREIGN PATENT DOCUMENTS

4236400A1  5/1994  Germany ..................... C07C 255/46

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

A phenylalkane amide compound having the formula (1):

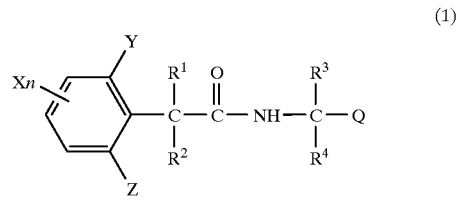

(1)

wherein $R^1$–$R^4$, X, n, Y, Z and Q are as defined herein. The compound is useful as an agricultural or horticultural fungicide.

13 Claims, No Drawings

PHENYLALKANE AMIDE DERIVATIVES AND AGRICULTURAL OR HORTICULTURAL FUNGICIDES

TITLE OF THE INVENTION

1. Field of the Invention

The present invention relates to novel phenylalkane amide derivatives and agricultural or horticultural fungicides containing the same as active ingredients.

2. Description of the Background

Heretofore, N-phenylacetaminonitriles such as N-(1-cyano-1-cyclopropylethyl)-2-(2,4-dichlorophenyl)acetamide and the like have been known as the intermediates of 3-arylpyrrolidin-2,4-diones (Japanese Patent Application, First Publication, No. Hei 6-220004 and Japanese Patent Application, First Publication, No. Hei 6-263731); however, the utility of the compounds as agricultural or horticultural fungicides are not known at all.

Recently, the fungicidal activities of the conventional fungicides may become degraded because of the emergence of resistant fungi after repeated use of the fungicides. For this reason, as well as because of environmental problems, it is desired to provide a novel fungicide which can efficiently control harmful fungi even at a low concentration.

In order to develop an agent having a superior fungicidal activity in comparison with the conventional fungicides, the present inventors have synthesized various novel phenylalkane amide derivatives and have carried out extensive research in connection with their effects on the biological activities of fungi. As a result, the present inventors have found that the novel compounds according to the present invention exhibit excellent fungicidal activities with regard to rice blast and the like, while at the same time do not hinder desirable plant growth.

DETAILED DESCRIPTION OF THE PREFERRED EMBODIMENTS

The present invention provides phenylalkane amide derivatives represented by Formula (1):

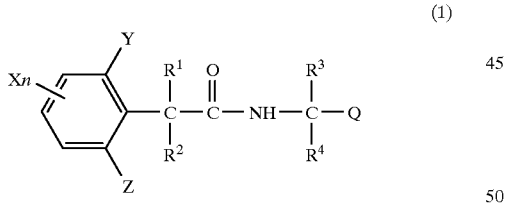

(1)

wherein $R^1$ represents a hydrogen atom or a $C_1$–$C_6$ alkyl group, $R^2$ represents a hydrogen atom, a $C_1$–$C_6$ alkyl group, a $C_3$–$C_6$ cycloalkyl group, or a $C_1$–$C_4$ haloalkyl group, $R^3$ and $R^4$ each independently represents a $C_1$–$C_6$ alkyl group, a $C_2$–$C_6$ alkenyl group, a $C_3$–$C_6$ cycloalkyl group, a $C_2$–$C_6$ alkoxyalkyl group, or a $C_1$–$C_4$ haloalkyl group, or $R^3$ and $R^4$, together with the carbon atom to which they are bonded, form a cycloalkyl group of 5-membered to 7-membered ring (which may be substituted by a $C_1$–$C_6$ alkyl group), Q represents a cyano group or a group of the formula: —$COR^5$ (wherein $R^5$ represents a hydroxy group, a $C_1$–$C_6$ alkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a phenoxy group, a benzyloxy group, an amino group, a $C_1$–$C_6$ alkylamino group, or a $C_1$–$C_6$ dialkylamino group), X represents a halogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a hydroxy group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, an aryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylthio group, a $C_1$–$C_6$ alkylsulfinyl group, a $C_1$–$C_6$ alkylsulfonyl group, a $C_1$–$C_4$ haloalkylthio group, an arylthio group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a group, a $C_1$–$C_4$ haloalkyl group, a $C_1$–$C_6$ alkoxy group, a cyano group, a nitro group, or a halogen atom), an arylsulfinyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an arylsulfonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an amino group, a $C_1$–$C_6$ alkylamino group, a $C_1$–$C_6$ dialkylamino group, a nitro group, a cyano group, or an aryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an aralkyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylcarbonyl group, an arylcarbonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroarylcarbonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a formyl group, or a $C_1$–$C_6$ alkoxycarbonyl group, Y and Z each independently represents a hydrogen atom, a $C_1$–$C_6$ alkyl group, a $C_1$–$C_4$ haloalkyl group, a $C_1$–$C_6$ alkoxy group, a cyano group, a nitro group, or a halogen atom, and n represents an integer of 0–3, with the exception that $R^3$ and $R^4$ represent a trifluoromethyl group at the same time, and with the proviso that when both $R^1$ and $R^2$ represent a hydrogen atoms at the same time, both Y and Z represent a hydrogen atom and n represents an integer of 1–3, as well as an agricultural or horticultural fungicide including the phenylalkane amide derivative as an active ingredient.

The terms employed in the present invention are defined in the following. In the present invention, for example, in the case of the expression "$C_1$–$C_6$", the group shown after "$C_1$–$C_6$" has 1 to 6 carbon atoms.

The term "$C_1-C_6$ alkyl group" is used herein to mean a straight-chain or branched alkyl group including, but not limited to, a methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, or the like.

As the "$C_3-C_6$ cycloalkyl group", there can be mentioned, for example, a cyclopropyl group, cyclopentyl group, cyclohexyl group, or the like.

The term "$C_1-C_4$ haloalkyl group" is used herein to mean a halogen-substituted straight-chain or branched alkyl group including, but not limited to, a fluoromethyl group, chloromethyl group, difluoromethyl group, dichloromethyl group, trifluoromethyl group, pentafluoroethyl group, or the like.

The term "$C_2-C_6$ alkenyl group" is used herein to mean a straight-chain or branched alkenyl group including, but not limited to, a vinyl group, 1-propenyl group, allyl group, isopropenyl group, 1-butenyl group, 2-butenyl group, or the like.

The term "$C_2-C_6$ alkynyl group" is used herein to mean a straight-chain or branched alkynyl group including, but not limited to, an ethynyl group, 1-propynyl group, 2-propynyl group, 1-butynyl group, 2-butynyl group, 3-butynyl group, 4-methyl-1-pentynyl group, 3-methyl-1-pentynyl group, or the like.

As the "aryl group", there can be mentioned, for example, a phenyl group, 1-naphthyl group, 2-naphthyl group, or the like.

As the "heteroaryl group", there can be mentioned, for example, a 2-pyridyl group, 3-pyridyl group, 4-pyridyl group, 2-furyl group, 3-furyl group, 2-thienyl group, 3-thienyl group, 1-pyrrolyl group, 2-pyrrolyl group, 3-pyrrolyl group, or the like.

The term "aralkyl group" is used herein to mean an aryl(having the same meaning as defined above)-substituted straight-chain or branched $C_1-C_3$ alkyl group including, but not limited to, a benzyl group, phenethyl group, 1-naphthylmethyl group, 2-naphthylmethyl group, or the like.

The term "halogen atom" is used herein to mean a fluorine atom, chlorine atom, bromine atom, or iodine atom.

The term "$C_1-C_6$ alkoxy group" is used herein to mean a straight-chain or branched alkoxy group including, but not limited to, a methoxy group, ethoxy group, n-propoxy group, isopropoxy group, n-butoxy group, isobutoxy group, sec-butoxy group, tert-butoxy group, n-pentyloxy group, isopentyloxy group, n-hexyloxy group, or the like.

The term "$C_2-C_6$ alkenyloxy group" is used herein to mean a straight-chain or branched alkenyloxy group including, but not limited to, an allyloxy group, isopropenyloxy group, 2-butenyloxy group, or the like.

The term "$C_2-C_6$ alkynyloxy group" is used herein to mean a straight-chain or branched alkynyloxy group including, for example, 2-propynyloxy group, 2-butynyloxy group, 3-butynyloxy group, or the like.

As the "$C_3-C_6$ cycloalkyloxy group", there can be mentioned, for example, a cyclopropyloxy group, cyclopentyloxy group, cyclohexyloxy group, or the like.

The term "$C_1-C_4$ haloalkoxy group" is used herein to mean a halogen-substituted straight-chain or branched alkoxy group including, but not limited to, a fluoromethoxy group, difluoromethoxy group, trifluoromethoxy group, pentafluoroethoxy group, or the like.

As the "aryloxy group", there can be mentioned, for example, a phenoxy group, 1-naphthyloxy group, 2-naphthyloxy group, or the like.

As the "heteroaryloxy group", there can be mentioned, for example, a 2-pyridyloxy group, 3-pyridyloxy group, 4-pyridyloxy group, 2-furyloxy group, 3-furyloxy group, 2-thienyloxy group, 3-thienyloxy group, or the like.

The term "aralkyloxy group" is used herein to mean an aryl-substituted straight-chain or branched $C_1-C_3$ alkoxy group including, but not limited to, a benzyloxy group, phenethyloxy group, or the like.

The term "$C_1-C_6$ alkylthio group" is used herein to mean a straight-chain or branched alkylthio group including, but not limited to, a methylthio group, ethylthio group, n-propylthio group, isopropylthio group, n-butylthio group, isobutylthio group, sec-butylthio group, tert-butylthio group, n-hexylthio group, or the like.

The term "$C_1-C_6$ alkylsulfinyl group" is used herein to mean a straight-chain or branched alkylsulfinyl group including, but not limited to, a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-hexylsulfinyl group, or the like.

The term "$C_1-C_6$ alkylsulfonyl group" is used herein to mean a straight-chain or branched alkylsulfonyl group including, but not limited to, a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-hexylsulfonyl group, or the like.

The term "$C_1-C_4$ haloalkylthio group" is used herein to mean a halogen-substituted straight-chain or branched alkylthio group including, but not limited to, a fluoromethylthio group, difluoromethylthio group, trifluoromethylthio group, pentafluoroethylthio group, or the like.

As the "arylthio group", there can be mentioned, for example, a phenylthio group, 1-naphthylthio group, 2-naphthylthio group, or the like.

As the "heteroarylthio group", there can be mentioned, for example, a 2-pyridylthio group, 3-pyridylthio group, 4-pyridylthio group, 2-furylthio group, 3-furylthio group, 2-thienylthio group, 3-thienylthio group, or the like.

As the "arylsulfinyl group", there can be mentioned, for example, a phenylsulfinyl group, 1-naphtylsulfinyl group, 2-naphtylsulfinyl group, or the like.

As the "arylsulfonyl group", there can be mentioned a phenylsulfonyl group, 1-naphthylsulfonyl group, 2-naphthylsulfonyl group, or the like.

The term "$C_1-C_6$ alkylamino group" is used herein to mean a straight-chain or branched alkylamino group including, for example, a methylamino group, ethylamino group, n-propylamino group, isopropylamino group, n-butylamino group, isobutylamino group, sec-butylamino group, tert-butylamino group, n-hexylamino group, or the like.

As the "$C_1-C_6$ dialkylamino group", there can be mentioned, for example, a dimethylamino group, diethylamino group, dipropylamino group, dibutylamino group, or the like.

The term "$C_1-C_6$ alkylcarbonyl group" is used herein to mean a straight-chain or branched alkylcarbonyl group including, for example, an acetyl group, propionyl group, butylyl group, isobutylyl group, or the like.

As the "arylcarbonyl group", there can be mentioned, for example, a benzoyl group, 1-naphthylcarbonyl group, 2-naphthylcarbonyl group, or the like.

As the "heteroarylcarbonyl group", there can be mentioned, for example, a 2-pyridylcarbonyl group, 3-pyridylcarbonyl group, 4-pyridylcarbonyl group, 2-furylcarbonyl group, 3-furylcarbonyl group, 2-thienylcarbonyl group, 3-thienylcarbonyl group, or the like.

The term "$C_1$–$C_6$ alkoxycarbonyl group" is used herein to mean a straight-chain or branched alkoxycarbonyl group including, for example, a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, n-hexyloxycarbonyl group, or the like.

The compounds represented by Formula (1) according to the present invention can exist in optical isomers by virtue of the presence of one or more chiral centers in a molecule. The present invention relates to all such diastereomers, enantiomers, and mixtures thereof.

The preferred compounds represented by Formula (1) according to the present invention are those in which:

$R^1$ represents a hydrogen atom or a methyl group, $R^2$ represents a hydrogen atom, a methyl group, or ethyl group, $R^3$ represents a methyl group, ethyl group, or n-propyl group, $R^4$ represents a methyl group, ethyl group, n-propyl group, isopropyl group, n-butyl group, isobutyl group, sec-butyl group, tert-butyl group, cyclopropyl group, cyclopentyl group, or dichloromethyl group, Q represents a cyano group, methoxycarbonyl group, ethoxycarbonyl group, n-propoxycarbonyl group, isopropoxycarbonyl group, n-butoxycarbonyl group, sec-butoxycarbonyl group, or carbamoyl group, X represents a fluorine atom, chlorine atom, bromine atom, iodine atom, a methyl group, ethyl group, isopropyl group, isobutyl group, sec-butyl group, tert-butyl group, cyclopentyl group, cyclohexyl group, trifluoromethyl group, methoxy group, ethoxy group, n-propoxy group, isopropoxy group, difluoromethoxy group, trifluoromethoxy group, phenoxy group, methylthio group, ethylthio group, isopropylthio group, dimethylamino group, diethylamino group, nitro group, cyano group, phenyl group, acetyl group, or benzoyl group, Y and Z each independently represents a hydrogen atom, or fluorine atom, and n represents an integer of 1–3.

Next, representative examples of the compounds represented by Formula (1) according to the present invention are listed in Tables 1~24. However, it should be understood that the present invention is not limited to these compounds. Compound Numbers given in the Tables will be referred to in the subsequent description.

In the tables, "Me" means a methyl group,

"Et" means an ethyl group,

"Pr-n" means an n-propyl group,

"Pr-i" means an isopropyl group,

"Bu-n" means an n-butyl group,

"Bu-i" means an isobutyl group,

"Bu-s" means a sec-butyl group,

"Bu-t" means a tert-butyl group,

"Pr-cyc" means a cyclopropyl group,

"Pen-cyc" means a cyclopentyl group,

"Ph" means a phenyl group,

"4-OPh(2-Cl)" means a 4-(2-chlorophenyl)oxy group,

"4-O(2-Py)" means a 4-(2-pyridyl)oxy group,

"4-O(5-$CF_3$,2-Py)" means a 4-(5-trifluoromethyl-2-pyridyl)oxy group,

"4-O(3-Py)" means a 4-(3-pyridyl)oxy group,

"4-O(4-Py)" means a 4-(4-pyridyl)oxy group,

"4-SPh(2-Cl)" means a 4-(2-chlorophenyl)thio group,

"4-S(O)Ph(2-Cl)" means a 4-(2-chlorophenyl)sulfinyl group,

"4-$SO_2$Ph(2-Cl)" means a 4-(2-chlorophenyl)sulfonyl group,

"4-S(2-Py)" means a 4-(2-pyridyl)thio group,

"4-Ph(4-$CF_3$)" means a 4-(4-trifluoromethylphenyl) group,

"4-(2-Py)" means a 4-(2-pyridyl) group,

"4-(2-Fur)" means a 4-(2-furyl) group,

"4-(2-Thi)" means a 4-(2-thienyl) group,

"4-COPh(2-Me)" means a 4-(2-methylbenzoyl) group,

"4-CO(3-Py)" means a 4-(3-pyridyl)carbonyl group,

"4-CO(2-Fur)" means a 4-(2-furyl)carbonyl group,

"4-CO(2-Thi)" means a 4-(2-thienyl)carbonyl group,

"4-$CH_2$Ph(3-Cl)" means a 4-(3-chlorobenzyl) group, and

"4-(1-Pyrr)" means a 4-(1-pyrrolyl) group.

TABLE 1

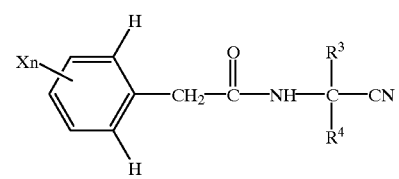

| Compound No. | Xn | $R^3$ | $R^4$ | Melting Point (°C.) |
|---|---|---|---|---|
| A-1 | 3-F | Me | Pr-i | |
| A-2 | 3-Cl | Me | Pr-i | 115–116 |
| A-3 | 3-Br | Me | Pr-i | |
| A-4 | 3-Me | Me | Pr-i | 104–105 |
| A-5 | 3-OMe | Me | Pr-i | |
| A-6 | 3-$CF_3$ | Me | Pr-i | 125–126 |
| A-7 | 3-CN | Me | Pr-i | |
| A-8 | 3-$NO_2$ | Me | Pr-i | 104–105 |
| A-9 | 3-OPh | Me | Pr-i | 136–137 |
| A-10 | 4-F | Me | Pr-i | 100–101 |
| A-11 | 4-Cl | Me | Me | |
| A-12 | 4-Cl | Me | Et | |
| A-13 | 4-Cl | Me | Pr-n | |
| A-14 | 4-Cl | Me | Pr-cyc | |
| A-15 | 4-Cl | Me | Pr-i | 122–123 |
| A-16 | 4-Cl | Me | $CHCl_2$ | 165–167 |
| A-17 | 4-Cl | Me | Bu-i | |
| A-18 | 4-Cl | Me | Bu-s | |
| A-19 | 4-Cl | Me | Bu-t | 151–152 |
| A-20 | 4-Cl | Et | Et | 125–127 |
| A-21 | 4-Cl | Et | Pr-n | |
| A-22 | 4-Cl | Et | Pr-i | |
| A-23 | 4-Br | Me | Pr-i | 125–126 |
| A-24 | 4-Br | Me | Bu-i | |
| A-25 | 4-Br | Me | Bu-s | |
| A-26 | 4-Br | Me | Bu-t | 164–165 |

TABLE 2

| Compound No. | Xn | R³ | R⁴ | Melting Point (°C.) |
|---|---|---|---|---|
| A-27 | 4-Br | Me | CHCl₂ | |
| A-28 | 4-Br | Et | Et | |
| A-29 | 4-Br | Et | Pr-i | |
| A-30 | 4-I | Me | Pr-i | 125–126 |
| A-31 | 3,4-Cl₂ | Me | Pr-i | 139–140 |
| A-32 | 3,5-Cl₂ | Me | Pr-i | |
| A-33 | 4-Me | Me | Pr-i | 100–101 |
| A-34 | 4-Et | Me | Pr-i | 104–105 |
| A-35 | 4-Pr-i | Me | Pr-i | 70–71 |
| A-36 | 4-Bu-i | Me | Pr-i | |
| A-37 | 4-C≡CMe | Me | Pr-i | |
| A-38 | 4-CH=CHMe | Me | Pr-i | |
| A-39 | 4-Bu-t | Me | Pen-cyc | |
| A-40 | 4-Bu-t | Me | CF₃ | |
| A-41 | 4-Bu-t | Me | Pr-i | 97–98 |
| A-42 | 4-Pen-cyc | Me | Bu-i | |
| A-43 | 4-Bu-t | Me | Bu-s | |
| A-44 | 4-Bu-t | Me | CH₂OMe | |
| A-45 | 4-Bu-t | Et | Et | |
| A-46 | 4-Bu-t | Et | Pr-n | |
| A-47 | 4-Bu-t | Et | Pr-i | |
| A-48 | 4-CF₃ | Me | —CH₂CH=CH₂ | |
| A-49 | 4-CF₃ | Me | Et | |
| A-50 | 4-CF₃ | Me | Pr-n | |
| A-51 | 4-CF₃ | Me | Pr-cyc | |
| A-52 | 4-CF₃ | Me | Pr-i | 104–105 |
| A-53 | 4-CF₃ | Me | CHCl₂ | |
| A-54 | 4-CP3 | Me | Bu-i | 94–96 |
| A-55 | 4-CF₃ | Me | Bu-s | |
| A-56 | 4-CF₃ | Me | Bu-t | 166–167 |

TABLE 3

| Compound No. | Xn | R³ | R⁴ | Melting Point (°C.) |
|---|---|---|---|---|
| A-57 | 4-CF₃ | Et | Et | 100–102 |
| A-58 | 4-CF₃ | Et | Pr-n | |
| A-59 | 4-CF₃ | Me | Pr-i | |
| A-60 | 4-OH | Me | Pr-i | 152–153 |
| A-61 | 4-OMe | Me | Pr-i | 107–108 |
| A-62 | 4-OEt | Me | Pr-i | 96–97 |
| A-63 | 4-OPr-i | Me | Pr-i | 76–77 |
| A-64 | 4-OBu-n | Me | Pr-i | 98–99 |
| A-65 | 4-OCH₂CH=CH₂ | Me | Pr-i | |
| A-66 | 4-OCH₂C≡CH | Me | Pr-i | |
| A-67 | 4-OPen-cyc | Me | Pr-i | |
| A-68 | 4-OCF₃ | Me | Pr-i | 85–86 |
| A-69 | 4-OCF₃ | Me | Bu-i | |
| A-70 | 4-OCF₃ | Me | Bu-s | |
| A-71 | 4-OCF₃ | Me | Bu-t | 152–154 |
| A-72 | 4-OCF₃ | Me | CF₃ | |
| A-73 | 4-OCF₃ | Et | Et | |
| A-74 | 3,4-(OMe)2 | Me | Pr-i | 89–90 |
| A-75 | 3,4,5-(OMe)3 | Me | Pr-i | 82–83 |
| A-76 | 4-OPh | Me | Pr-i | 139–141 |
| A-77 | 4-O(2-Py) | Me | Pr-i | |
| A-78 | 4-O(5-CF₃, 2-Py) | Me | Pr-i | 132–133 |
| A-79 | 4-O(3-Py) | Me | Pr-i | |
| A-80 | 4-O(4-Py) | Me | Pr-i | |
| A-81 | 4-SMe | Me | Pr-i | 122–123 |
| A-82 | 4-SO₂Me | Me | Pr-i | 116–118 |
| A-83 | 4-SPh | Me | Pr-i | |
| A-84 | 4-SO₂Ph | Me | Pr-i | |
| A-85 | 4-NH₂ | Me | Pr-i | |
| A-86 | 4-N(Me)₂ | Me | Pr-i | 147–148 |

TABLE 4

| Compound No. | Xn | R³ | R⁴ | Melting Point (°C.) |
|---|---|---|---|---|
| A-87 | 4-Ph | Me | Pr-i | 151–152 |
| A-88 | 4-S(2-Py) | Me | Pr-i | |
| A-89 | 4-S(4-Py) | Me | Pr-i | |
| A-90 | 4-Ph | Me | Bu-s | |
| A-91 | 4-Ph | Me | Bu-t | |
| A-92 | 4-Ph | Et | Et | 169–170 |
| A-93 | 4-Ph(4-CF₃) | Me | Pr-i | |
| A-94 | 4-Ph(2-CN) | Me | Pr-i | |
| A-95 | 4-Ph(3-NO₂) | Me | Pr-i | |
| A-96 | 4-Ph(4-Cl) | Me | Pr-i | |
| A-97 | 4-Ph(4-Me) | Me | Pr-i | |
| A-98 | 4-Ph(4-OMe) | Me | Pr-i | |
| A-99 | 4-(2-Py) | Me | Pr-i | |
| A-100 | 4-(3-Py) | Me | Pr-i | |
| A-101 | 4-(4-Py) | Me | Pr-i | |
| A-102 | 4-(2-Fur) | Me | Pr-i | |
| A-103 | 4-(2-Thi) | Me | Pr-i | |
| A-104 | 4-CN | Me | Pr-i | 126–127 |
| A-105 | 4-NO₂ | Me | Pr-i | 135–136 |
| A-106 | 4-COMe | Me | Pr-i | |
| A-107 | 4-COPh | Me | Pr-i | 106–108 |
| A-108 | 4-COPh(2-Me) | Me | Pr-i | |
| A-109 | 4-COPh(3-OMe) | Me | Pr-i | |
| A-110 | 4-COPh(4-Cl) | Me | Pr-i | |
| A-111 | 4-CO(2-Fur) | Me | Pr-i | |
| A-112 | 4-CO(2-Thi) | Me | Pr-i | |
| A-113 | 4-CO(3-Py) | Me | Pr-i | |
| A-114 | 4-CO₂Me | Me | Pr-i | |
| A-115 | 4-CH₂Ph | Me | Pr-i | |
| A-116 | 4-CH₂CH₂Ph | Me | Pr-i | |
| A-117 | 4-I | Me | Bu-t | 170–172 |

TABLE 5

Xn-C₆H₃(H)(H)-CH₂-C(=O)-NH-C(R³)(R⁴)-COR⁵

| Compound No. | Xn | R³ | R⁴ | R⁵ | Melting Point (°C.) |
|---|---|---|---|---|---|
| B-1 | 3-Cl | Me | Pr-i | OMe | |
| B-2 | 3-Me | Me | Pr-i | OMe | |
| B-3 | 3-OMe | Me | Pr-i | OMe | |
| B-4 | 3-CF₃ | Me | Pr-i | OMe | |
| B-5 | 3-NO₂ | Me | Pr-i | OMe | |
| B-6 | 4-Cl | Me | Pr-i | OMe | 142–143 |
| B-7 | 4-Cl | Me | Pr-i | OEt | 107–109 |
| B-8 | 4-Cl | Me | Pr-i | OPr-i | 111–112 |
| B-9 | 4-Cl | Me | Pr-i | OCH₂Ph | |
| B-10 | 4-Cl | Me | Pr-i | OCH₂CH=CH₂ | |
| B-11 | 4-Cl | Me | Pr-i | OCH₂C≡CH | |
| B-12 | 4-Cl | Me | Pr-i | OPh | |
| B-13 | 4-Cl | Me | Pr-i | NH₂ | 203–204 |
| B-14 | 4-Cl | Me | Pr-i | N(Me)₂ | |
| B-15 | 4-Cl | Me | Pr-i | Me | |
| B-16 | 4-Cl | Et | Et | OMe | |
| B-17 | 4-Cl | Et | Et | OEt | |
| B-18 | 4-Cl | Et | Et | OPr-i | |
| B-19 | 4-Cl | Et | Et | OCH₂Ph | |
| B-20 | 4-Cl | Et | Et | OCH₂CH=CH₂ | |
| B-21 | 4-Cl | Et | Et | OCH₂C≡CH | |
| B-22 | 4-Cl | Et | Et | OPh | |
| B-23 | 4-Cl | Et | Et | NH₂ | |

TABLE 5-continued

Structure: Xn-phenyl-CH2-C(=O)-NH-C(R3)(R4)-COR5 (with 2,6-H on phenyl)

| Compound No. | Xn | R³ | R⁴ | R⁵ | Melting Point (°C.) |
|---|---|---|---|---|---|
| B-24 | 4-Cl | Et | Et | N(Me)₂ | |
| B-25 | 4-Cl | Et | Et | Me | |
| B-26 | 4-Cl | Me | Bu-t | OMe | |

TABLE 6

| Compound No. | Xn | R³ | R⁴ | R⁵ | Melting Point (°C.) |
|---|---|---|---|---|---|
| B-27 | 4-Cl | Me | Bu-t | OEt | |
| B-28 | 4-I | Me | Pr-i | OMe | |
| B-29 | 4-I | Me | Pr-i | OEt | |
| B-30 | 4-I | Me | Pr-i | NH₂ | |
| B-31 | 4-I | Et | Et | OMe | |
| B-32 | 4-I | Et | Et | OPr-i | |
| B-33 | 4-I | Me | Bu-t | OMe | |
| B-34 | 4-CF₃ | Me | Pr-i | OMe | 154–155 |
| B-35 | 4-CF₃ | Me | Pr-i | OEt | 98–99 |
| B-36 | 4-CF₃ | Me | Pr-i | OPr-i | 122–123 |
| B-37 | 4-CF₃ | Me | Pr-i | OCH₂Ph | |
| B-38 | 4-CF₃ | Me | Pr-i | OCH₂CH=CH₂ | |
| B-39 | 4-CF₃ | Me | Pr-i | OH | |
| B-40 | 4-CF₃ | Me | Pr-i | OPen-cyc | |
| B-41 | 4-CF₃ | Me | Pr-i | NH₂ | 218–220 |
| B-42 | 4-CF₃ | Me | Pr-i | N(Me)₂ | |
| B-43 | 4-CF₃ | Me | Pr-i | Me | |
| B-44 | 4-CF₃ | Et | Et | OMe | |
| B-45 | 4-CF₃ | Et | Et | OEt | |
| B-46 | 4-CF₃ | Et | Et | OPr-i | |
| B-47 | 4-CF₃ | Et | Et | OPen-cyc | |
| B-48 | 4-CF₃ | CH₂Cl | CH₂Cl | OMe | |
| B-49 | 4-CF₃ | Pr-n | Pr-n | OMe | |
| B-50 | 4-CF₃ | Et | Et | NH₂ | |
| B-51 | 4-CF₃ | Et | Et | Me | |
| B-52 | 4-CF₃ | Me | Bu-t | OMe | |
| B-53 | 4-CF₃ | Me | Bu-t | OEt | |
| B-54 | 4-CF₃ | Me | Bu-t | OPr-i | |
| B-55 | 4-CF₃ | Me | Bu-t | OPen-cyc | |
| B-56 | 4-CF₃ | Me | Bu-t | OCH₂CH=CH₂ | |

TABLE 7

| Compound No. | Xn | R³ | R⁴ | R⁵ | Melting Point (°C.) |
|---|---|---|---|---|---|
| B-57 | 4-CF₃ | Me | Bu-t | OCH₂C≡CH | |
| B-58 | 4-CF₃ | Me | Bu-t | NH₂ | |
| B-59 | 4-CF₃ | Me | Bu-t | NHMe | |
| B-60 | 4-CF₃ | Me | Bu-t | Pr-i | |
| B-61 | 4-Bu-t | Me | Pr-i | OMe | |
| B-62 | 4-Bu-t | Me | Pr-i | OEt | |
| B-63 | 4-Bu-t | Me | Pr-i | OPr-i | |
| B-64 | 4-Bu-t | Me | Pr-i | OCH₂Ph | |
| B-65 | 4-Bu-t | Me | Pr-i | OCH₂CH=CH₂ | |
| B-66 | 4-Bu-t | Me | Pr-i | OCH₂C≡CH | |
| B-67 | 4-Bu-t | Me | Pr-i | OPh | |
| B-68 | 4-Bu-t | Me | Pr-i | NH | |
| B-69 | 4-Bu-t | Me | Pr-i | N(Me)₂ | |
| B-70 | 4-Bu-t | Me | Pr-i | Me | |
| B-71 | 4-Bu-t | Et | Et | OMe | |
| B-72 | 4-Bu-t | Et | Et | OEt | |
| B-73 | 4-Bu-t | Et | Et | OPr-i | |
| B-74 | 4-Bu-t | Et | Et | NH₂ | |
| B-75 | 4-Pr-i | Et | Et | OMe | |
| B-76 | 4-Pr-i | Et | Et | OEt | |
| B-77 | 4-Pr-i | Et | Et | NH₂ | |
| B-78 | 4-Pr-i | Et | Et | N(Et)₂ | |
| B-79 | 4-Pr-i | Me | Pr-i | OMe | |
| B-80 | 4-Pr-i | Me | Pr-i | OEt | |
| B-81 | 4-Pr-i | Me | Pr-i | OPr-i | |
| B-82 | 4-Pr-i | Me | Pr-i | NH₂ | |
| B-83 | 4-Pr-i | Me | Pr-i | Me | |
| B-84 | 4-Br | Me | Pr-i | OMe | |
| B-85 | 4-Br | Me | Pr-i | OEt | |
| B-86 | 4-Br | Me | Pr-i | OPr-i | |

TABLE 8

| Compound No. | Xn | R³ | R⁴ | R⁵ | Melting Point (°C.) |
|---|---|---|---|---|---|
| B-87 | 4-Br | Me | Pr-i | OCH₂Ph | |
| B-88 | 4-Br | Me | Pr-i | OCH₂CH=CH₂ | |
| B-89 | 4-Br | Me | Pr-i | OCH₂C≡CH | |
| B-90 | 4-Br | Me | Pr-i | OPh | |
| B-91 | 4-Br | Me | Pr-i | NH₂ | |
| B-92 | 4-Br | Me | Pr-i | N(Me)₂ | |
| B-93 | 4-Br | Me | Pr-i | Me | |
| B-94 | 4-Br | Et | Et | OMe | |
| B-95 | 4-Br | Et | Et | OEt | |
| B-96 | 4-Br | Et | Et | OPr-i | |
| B-97 | 4-Br | Et | Et | OPen-cyc | |
| B-98 | 4-Br | Et | Et | OCH₂CH=CH₂ | |
| B-99 | 4-Br | Et | Et | NHPr-i | |
| B-100 | 4-Br | Et | Et | NH₂ | |
| B-101 | 4-Br | Et | Et | Me | |
| B-102 | 4-Br | Me | Bu-t | OMe | |
| B-103 | 4-Br | Me | Bu-t | OEt | |
| B-104 | 4-Br | Me | Bu-t | OPr-i | |
| B-105 | 4-Br | Me | Bu-t | OPen-cyc | |
| B-106 | 4-Br | Me | Bu-t | NH₂ | |
| B-107 | 4-Br | Me | Bu-t | NHMe | |
| B-108 | 4-Br | Me | Bu-t | Me | |
| B-109 | 4-OMe | Me | Pr-i | OMe | |
| B-110 | 4-OMe | Me | Pr-i | OEt | |
| B-111 | 4-OMe | Me | Pr-i | OPr-i | |
| B-112 | 4-OMe | Et | Et | OEt | |
| B-113 | 4-OMe | Et | Et | OPr-i | |
| B-114 | 4-Ph | Me | Pr-i | OMe | |
| B-115 | 4-Ph | Me | Pr-i | OEt | |
| B-116 | 4-Ph | Me | Pr-i | OMe | 153–154 |

TABLE 9

| Compound No. | Xn | R³ | R⁴ | R⁵ | Melting Point (°C.) |
|---|---|---|---|---|---|
| B-117 | 4-Ph | Me | Pr-i | OEt | |
| B-118 | 4-Ph | Me | Pr-i | OPr-i | |
| B-119 | 4-Ph | Me | Pr-i | OCH₂CH=CH₂ | |
| B-120 | 4-Ph | Me | Pr-i | OCH₂C≡CH | |
| B-121 | 4-Ph | Me | Pr-i | NH₂ | |
| B-122 | 4-Ph | Me | Pr-i | NHMe | |
| B-123 | 4-Ph | Me | Pr-i | Me | |
| B-124 | 4-Ph | Et | Et | OMe | |
| B-125 | 4-Ph | Et | Et | OEt | |
| B-126 | 4-SPh | Et | Et | OMe | |

TABLE 9-continued

| Compound No. | Xn | R³ | R⁴ | R⁵ | Melting Point (°C.) |
|---|---|---|---|---|---|
| B-127 | 4-S(O)Ph | Et | Et | OMe | |
| B-128 | 4-SO₂Ph | Et | Et | OMe | |
| B-129 | 4-Ph | Et | Et | NH₂ | |
| B-130 | 4-Ph | Et | Et | Pr-i | |
| B-131 | 4-Ph | Me | Bu-t | OMe | |
| B-132 | 4-Ph | Me | Bu-t | OEt | |
| B-133 | 4-Ph | Me | Bu-t | OPr-i | |
| B-134 | 4-Ph | Me | Bu-t | OPen-cyc | |
| B-135 | 4-Ph | Me | Bu-t | OMe | |
| B-136 | 4-OPr-i | Me | Pr-i | OMe | |
| B-137 | 4-OPr-i | Me | Pr-i | OEt | |
| B-138 | 4-OPr-i | Me | Pr-i | OPr-i | |
| B-139 | 4-OPr-i | Me | Pr-i | OPen-cyc | |
| B-140 | 4-OCF₃ | Me | Bu-t | OMe | 125–126 |
| B-141 | 4-OCF₃ | Me | Pr-i | OMe | |
| B-142 | 4-OCF₃ | Me | Pr-i | OPen-cyc | |
| B-143 | 4-OCF₃ | Me | Pr-i | NH₂ | |
| B-144 | 4-SMe | Me | Pr-i | OMe | |
| B-145 | 4-SMe | Me | Pr-i | OEt | |
| B-146 | 4-SMe | Me | Pr-i | OPr-i | |

TABLE 10

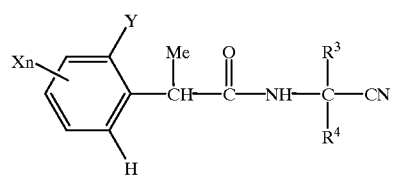

| Compound No. | Xn | Y | R³ | R⁴ | Melting Point (°C.) or Refractive Index ($n_D^{20}$) |
|---|---|---|---|---|---|
| C-1 | — | H | Me | Me | 132–133 |
| C-2 | — | H | Me | Pr-cyc | 71–73 |
| C-3 | — | H | Me | Pr-i | 108–110 |
| C-4 | — | H | Et | Et | |
| C-5 | — | Cl | Me | Pr-i | |
| C-6 | — | Me | Me | Pr-i | |
| C-7 | — | OMe | Me | Pr-i | |
| C-8 | — | CF₃ | Me | Pr-i | |
| C-9 | — | CN | Et | Et | |
| C-10 | — | NO₂ | Et | Et | |
| C-11 | — | Me | Et | Et | |
| C-12 | 4-Cl | F | Me | Pr-i | |
| C-13 | 4-Cl | Cl | Me | Pr-i | 129–130 |
| C-14 | 4-Cl | Cl | Et | Et | |
| C-15 | 3-F | H | Me | Pr-i | |
| C-16 | 3-Cl | H | Me | Pr-i | 1.5115 |
| C-17 | 3-Br | H | Me | Pr-i | 1.5242 |
| C-18 | 3-Me | H | Me | Pr-i | 71–72 |
| C-19 | 3-Me | H | Me | Pr-i | 74–76 |
| C-20 | 3-OMe | H | Me | Pr-i | |
| C-21 | 3-CF₃ | H | Me | Pr-i | 1.4660 |
| C-22 | 3-CF₃ | H | Me | Pr-i | 124–125 |
| C-23 | 3-NO₂ | H | Me | Pr-i | |
| C-24 | 3-COPh | H | Me | Pr-i | 117–119 |
| C-25 | 3-COPh | H | Me | Pr-i | 1.5550 |
| C-26 | 3-CH₂Ph | H | Me | Pr-i | |

TABLE 11

| Compound No. | Xn | Y | R³ | R⁴ | Melting Point (°C.) or Refractive Index ($n_D^{20}$) |
|---|---|---|---|---|---|
| C-27 | 4-F | H | Me | Pr-i | 127–129 |
| C-28 | 4-F | H | Me | Pr-i | 124–127 |
| C-29 | 4-Cl | H | Me | Me | 148–149 |
| C-30 | 4-Cl | H | —(CH₂)₄— | | 123–124 |
| C-31 | 4-Cl | H | Me | Pr-n | |
| C-32 | 4-Cl | H | Me | Pr-cyc | 1.5318 |
| C-33 | 4-Cl | H | Me | Pr-i | 102–106 |
| C-34 | 4-Cl | H | Me | Pr-i | 125–126 |
| C-35 | 4-Cl | H | Me | Pr-i | 133–134 |
| C-36 | 4-Cl | H | Me | CF₃ | |
| C-37 | 4-Cl | H | Me | Bu-s | |
| C-38 | 4-Cl | H | Me | Bu-i | 1.5141 |
| C-39 | 4-Cl | H | Me | Bu-t | 122–124 |
| C-40 | 4-Cl | H | Me | Bu-t | 158–159 |
| C-41 | 4-Cl | H | Et | Et | 77–79 |
| C-42 | 4-Cl | H | Et | Et | 77–79 |
| C-43 | 4-Cl | H | Et | Et | 77–79 |
| C-44 | 4-Cl | H | Et | Pr-i | 90–93 |
| C-45 | 4-Br | H | Me | Pr-n | |
| C-46 | 4-Br | H | Me | Pen-cyc | |
| C-47 | 4-Br | H | Me | Pr-i | 130–131 |
| C-48 | 4-Br | H | Me | Pr-i | 121–123 |
| C-49 | 4-Br | H | Me | Pr-i | 87–89 |
| C-50 | 4-Br | H | Me | Bu-s | |
| C-51 | 4-Br | H | Me | Bu-t | 143–144 |
| C-52 | 4-Br | H | Me | Bu-t | 150–152 |
| C-53 | 4-Br | H | Et | Et | 97–99 |
| C-54 | 4-I | H | Me | Pr-i | 116–118 |
| C-55 | 4-I | H | Me | Pr-i | 120–122 |
| C-56 | 4-I | H | Me | Pr-i | 95–98 |

TABLE 12

| Compound No. | Xn | Y | R³ | R⁴ | Melting Point (°C.) or Refractive Index ($n_D^{20}$) |
|---|---|---|---|---|---|
| C-57 | 3,5-Cl₂ | H | Me | Pr-i | |
| C-58 | 4-Me | H | —CH₂CH=CH₂ | —CH₂CH=CH₂ | |
| C-59 | 4-Me | H | —(CH₂)₄— | | |
| C-60 | 4-Me | H | Me | Pr-n | |
| C-61 | 4-Me | H | Me | Pen-cyc | |
| C-62 | 4-Me | H | Me | Pr-i | 136–137 |
| C-63 | 4-Me | H | Me | Pr-i | 102–103 |
| C-64 | 4-Me | H | Me | Pr-i | 89–90 |
| C-65 | 4-Me | H | Me | Bu-s | |
| C-66 | 4-Me | H | Me | Bu-t | 94–97 |
| C-67 | 4-Me | H | Me | Bu-t | 103–105 |
| C-68 | 4-Me | H | Et | Et | 99–103 |
| C-69 | 4-Me | H | Et | Pr-n | |
| C-70 | 4-Me | H | Et | Pr-i | 134–137 |
| C-71 | 4-Et | H | Me | Pr-i | 122–123 |
| C-72 | 4-Et | H | Me | Pr-i | 109–110 |
| C-73 | 4-Pr-i | H | Me | Pr-i | 109–111 |
| C-74 | 4-Pr-i | H | Me | Pr-i | 101–102 |
| C-75 | 4-Bu-i | H | Me | Pr-i | 110–111 |
| C-76 | 4-Bu-i | H | Me | Pr-i | 84–85 |
| C-77 | 4-Bu-t | H | —(CH₂)₆— | | |
| C-78 | 4-Bu-t | H | | Et | |
| C-79 | 4-Bu-t | H | Me | Pr-n | |
| C-80 | 4-Bu-t | H | Me | Pr-cyc | |
| C-81 | 4-Bu-t | H | Me | Pr-i | 136–137 |
| C-82 | 4-Bu-t | H | Me | Pr-i | 140–141 |
| C-83 | 4-Bu-t | H | Me | CF₃ | |
| C-84 | 4-Bu-t | H | Me | Bu-s | |
| C-85 | 4-Bu-t | H | Me | Bu-i | |
| C-86 | 4-Bu-t | H | Me | Bu-t | |

TABLE 13

| Compound No. | Xn | Y | $R^3$ | $R^4$ | Melting Point (°C.) or Refractive Index ($n_D^{20}$) |
|---|---|---|---|---|---|
| C-87 | 4-Et | H | Et | Et | 70–72 |
| C-88 | 4-Et | H | Me | Bu-t | 101–103 |
| C-89 | 4-Et | H | Me | Bu-t | 102–103 |
| C-90 | 4-CF₃ | H | —(CH₂)₅— | | |
| C-91 | 4-CF₃ | H | Me | Et | |
| C-92 | 4-CF₃ | H | Me | Pr-cyc | 92–94 |
| C-93 | 4-CF₃ | H | Me | Pr-cyc | 114–117 |
| C-94 | 4-CF₃ | H | Me | Pr-i | 121–124 |
| C-95 | 4-CF₃ | H | Me | Pr-i | 126–127 |
| C-96 | 4-CF₃ | H | Me | CHCl₂ | |
| C-97 | 4-CF₃ | H | Me | Bu-s | |
| C-98 | 4-CF₃ | H | Me | Bu-i | |
| C-99 | 4-CF₃ | H | Me | Bu-t | 120–121 |
| C-100 | 4-CF₃ | H | Me | Bu-t | 163–164 |
| C-101 | 4-CF₃ | H | Et | Et | 87–88 |
| C-102 | 4-CF₃ | H | Et | Pr-i | 100–103 |
| C-103 | 4-CF₃ | H | Et | Pr-i | 106–107 |
| C-104 | 4-CH₂Ph | H | Me | Pr-i | |
| C-105 | 4-OH | H | Me | Pr-i | |
| C-106 | 4-OMe | H | Ale | Pr-i | 108–109 |
| C-107 | 4-OMe | H | Me | Pr-i | 99–100 |
| C-108 | 4-OEt | H | Me | Pr-i | 93–94 |
| C-109 | 4-OEt | H | Me | Pr-i | 112–113 |
| C-110 | 4-OPr-i | H | Me | Pr-n | |
| C-111 | 4-OPr-i | H | —(CH₂)₅— | | |
| C-112 | 4-OPr-i | H | Me | Pr-i | 111–112 |
| C-113 | 4-OPr-i | H | Me | Pr-i | 128–129 |
| C-114 | 4-OCHF₂ | H | Me | Pr-i | 74–80 |
| C-115 | 4-OCHF₂ | H | Me | Pr-i | 98–102 |
| C-116 | 4-OCHF₂ | H | Et | Et | 1.4959 |

TABLE 14

| Compound No. | Xn | Y | $R^3$ | $R^4$ | Melting Point (°C.) or Refractive Index ($n_D^{20}$) |
|---|---|---|---|---|---|
| C-117 | 4-OCH₂CF₃ | H | Me | Pr-i | 68–70 |
| C-118 | 4-OCH₂CF₃ | H | Me | Pr-i | 98–101 |
| C-119 | 4-OPr-i | H | Et | Et | 90–93 |
| C-120 | 4-OPr-n | H | Me | Pr-i | 105–107 |
| C-121 | 4-OPen-cyc | H | Me | Pr-i | 108–110 |
| C-122 | 4-OCF₃ | H | Me | Pr-i | 97–98 |
| C-123 | 4-OCF₃ | H | Me | Pr-i | 122–124 |
| C-124 | 4-OCF₃ | H | Me | CF₃ | |
| C-125 | 4-OCF₃ | H | Et | Et | 1.4776 |
| C-126 | 4-OCF₃ | H | Me | Bu-t | |
| C-127 | 3,4-(OMe)₂ | H | Me | Pr-i | |
| C-128 | 3,4,5-(OMe)₃ | H | Me | Pr-i | |
| C-129 | 4-OPh | H | Me | Pr-i | 120–122 |
| C-130 | 4-OPh | H | Me | Pr-i | 129–131 |
| C-131 | 4-SMe | H | Me | Pr-i | 90–93 |
| C-132 | 4-S(O)Me | H | Me | Bu-t | |
| C-133 | 4-SPr-i | H | Et | Et | |
| C-134 | 4-SPh | H | Me | Pr-i | |
| C-135 | 4-SO₂Me | H | Me | Pr-i | |
| C-136 | 4-SO₂Ph | H | Me | Pr-i | |
| C-137 | 4-NH₂ | H | Me | Pr-i | 1.5364 |
| C-138 | 4-N(Me)₂ | H | Me | Pr-i | |
| C-139 | 4-NHPr-i | H | Me | Pr-i | |
| C-140 | 4-Ph | H | Me | Pr-i | 142–143 |
| C-141 | 4-Ph | H | Me | Pr-i | 149–150 |
| C-142 | 4-Ph | H | Et | Et | |
| C-143 | 4-Ph | H | Me | Bu-s | |
| C-144 | 4-Ph | H | Me | Bu-t | |
| C-145 | 4-OPh(2-Cl) | R | Me | Pr-i | |
| C-146 | 4-CH₂Ph(3-Cl) | H | Me | Pr-i | |

TABLE 15

| Compound No. | Xn | Y | $R^3$ | $R^4$ | Melting Point (°C.) or Refractive Index ($n_D^{20}$) |
|---|---|---|---|---|---|
| C-147 | 4-Ph(4-Cl) | H | Me | Pr-i | |
| C-148 | 4-Ph(2-Me) | H | Me | Pr-i | |
| C-149 | 4-OPh(3-Me) | H | Me | Pr-i | |
| C-150 | 4-CH₂Ph(4-Me) | H | Me | Pr-i | |
| C-151 | 4-CH₂Ph(2-OMe) | H | Me | Pr-i | |
| C-152 | 4-Ph(3-OMe) | H | Me | Pr-i | |
| C-153 | 4-OPh(4-OMe) | H | Me | Pr-i | |
| C-154 | 4-(2-Py) | H | Me | Pr-i | |
| C-155 | 4-(3-Py) | H | Me | Pr-i | |
| C-156 | 4-(4-Py) | H | Me | Pr-i | |
| C-157 | 4-CN | H | Me | Pr-i | 148–149 |
| C-158 | 4-CN | H | Me | Pr-i | 124–125 |
| C-159 | 4-NO₂ | H | Me | Pr-i | 121–123 |
| C-160 | 4-COMe | H | Me | Pr-i | |
| C-161 | 4-COPh | H | Me | Pr-i | 105–108 |
| C-162 | 4-COPh | H | Me | Pr-i | 154–157 |
| C-163 | 4-COPh(3-Me) | H | Me | Pr-i | |
| C-164 | 4-COPh(4-Cl) | H | Me | Pr-i | |
| C-165 | 4-CO(2-Thi) | H | Me | Pr-i | 144–146 |
| C-166 | 4-CO(2-Thi) | H | Me | Pr-i | 115–117 |
| C-167 | 4-CO₂Me | H | Me | Pr-i | |
| C-168 | 4-CO₂Pr-i | H | Me | Pr-i | |
| C-169 | 3,4-Cl₂ | H | Me | Pr-i | 100–102 |
| C-170 | 3,4-Cl₂ | H | Me | Pr-i | 171–173 |
| C-171 | 3,4-Cl₂ | H | Me | Bu-t | 134–136 |
| C-172 | 3,4-Cl₂ | H | Me | Bu-t | 157–158 |
| C-173 | 3,4-Cl₂ | H | Et | Et | 61–63 |
| C-174 | 3-Cl, 4-OMe | H | Me | Pr-i | 1.5260 |
| C-175 | 3-Cl, 4-OMe | H | Me | Pr-i | 125–127 |
| C-176 | 3-Cl, 4-OMe | H | Me | Pr-i | 88–90 |

TABLE 16

| Compound No. | Xn | Y | $R^3$ | $R^4$ | Melting Point (°C.) or Refractive Index ($n_D^{20}$) |
|---|---|---|---|---|---|
| C-177 | 3,4-(Me)₂ | H | Me | Pr-i | 100–101 |
| C-178 | 3,4-(Me)₂ | H | Me | Pr-i | 128–130 |
| C-179 | 3,4-(Me)₂ | H | Me | Bu-t | 67–69 |
| C-180 | 3,4-(Me)₂ | H | Me | Bu-t | 100–101 |
| C-181 | 4-C≡CMe | H | Me | Pr-i | 106–108 |
| C-182 | 4-C≡CMe | H | Me | Pr-i | 78–80 |
| C-183 | 4-CH=CH₂ | H | Me | Pr-i | |
| C-184 | 4-SMe | H | Me | Bu-t | 91–94 |
| C-185 | 4-SMe | H | Me | Bu-t | 108–110 |
| C-186 | 4-SMe | H | Et | Et | 77–78 |
| C-187 | 4-I | H | Me | Bu-t | 129–130 |
| C-188 | 4-I | H | Me | Bu-t | 132–133 |
| C-189 | 4-I | H | Me | Pr-cyc | 118–120 |
| C-190 | 4-I | H | Me | Pr-cyc | 142–144 |
| C-191 | 4-I | H | Et | Et | 105–108 |
| C-192 | 4-OCF₃ | H | Me | Bu-t | 116–119 |
| C-193 | 4-(1-Pyrr) | H | Me | Pr-i | 119–120 |
| C-194 | 4-(1-Pyrr) | H | Me | Pr-i | 156–158 |
| C-195 | 4-(1-Pyrr) | H | Me | Pr-i | 123–125 |
| C-196 | 4-Cl | H | Me | Pr-i | 102–104 |
| C-197 | 4-Cl | H | Me | Pr-i | 120–121 |
| C-198 | 4-Cl | H | Me | Pr-i | 107–109 |
| C-199 | 4-Cl | H | Me | Pr-i | 121–122 |
| C-200 | 4-OMe | H | Me | Bu-t | 1.5219 |
| C-201 | 4-OMe | H | Me | Bu-t | 88–90 |
| C-202 | 4-OMe | H | Me | Bu-t | 67–68 |

TABLE 17

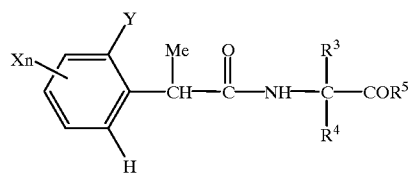

| Compound No. | Xn | Y | R³ | R⁴ | R⁵ | Melting Point (°C.) |
|---|---|---|---|---|---|---|
| D-1 | — | H | Me | Pr-i | OMe | |
| D-2 | — | H | Me | Pr-i | OEt | |
| D-3 | — | R | Me | Pr-i | OPr-i | |
| D-4 | — | H | Me | Pr-i | NH | |
| D-5 | — | F | Me | Pr-i | OMe | |
| D-6 | — | Cl | Me | Pr-i | OMe | |
| D-7 | 4-Cl | F | Me | Pr-i | OMe | |
| D-8 | 4-Cl | Cl | Me | Pr-i | OMe | |
| D-9 | 3-Me | H | Me | Pr-i | OMe | |
| D-10 | 3-Me | H | Me | Pr-i | OEt | |
| D-11 | 3-Me | H | Me | Pr-i | OPr-i | |
| D-12 | 3-Me | H | Me | Pr-i | NH₂ | |
| D-13 | 3-Cl | H | Me | Pr-i | OMe | |
| D-14 | 3-Cl | H | Me | Pr-i | OEt | |
| D-15 | 3-Cl | H | Me | Pr-i | OPr-i | |
| D-16 | 3-Cl | H | Me | Pr-i | NH₂ | |
| D-17 | 3-NO₂ | H | Me | Pr-i | OMe | |
| D-18 | 4-F | H | Me | Pr-i | OMe | |
| D-19 | 4-Cl | H | Me | Pr-i | OMe | 120–123 |
| D-20 | 4-Cl | H | Me | Pr-i | OEt | 115–118 |
| D-21 | 4-Cl | H | Me | Pr-i | OPr-i | 124–126 |
| D-22 | 4-Cl | H | Me | Pr-i | OCH₂Ph | |
| D-23 | 4-Cl | H | Me | Pr-i | OCH₂CH=CH₂ | |
| D-24 | 4-Cl | H | Me | Pr-i | OCH₂C≡CH | |
| D-25 | 4-Cl | H | Me | Pr-i | Me | |
| D-26 | 4-Cl | H | Me | Pr-i | NH₂ | 136–137 |

TABLE 18

| Compound No. | Xn | Y | R³ | R⁴ | R⁵ | Melting Point (°C.) |
|---|---|---|---|---|---|---|
| D-27 | 4-Cl | H | Me | Pr-i | N(Me)₂ | |
| D-28 | 4-Cl | H | Et | Et | OMe | 98–99 |
| D-29 | 4-Cl | H | Et | Et | OEt | 85–87 |
| D-30 | 4-Cl | H | Et | Et | OPr-i | |
| D-31 | 4-Cl | H | Et | Et | Me | |
| D-32 | 4-Cl | H | Et | Et | NH₂ | 116–118 |
| D-33 | 4-Cl | H | Et | Et | N(Me)₂ | |
| D-34 | 4-Cl | H | Me | Bu-t | OMe | 122–123 |
| D-35 | 4-Cl | H | Me | Bu-t | OEt | |
| D-36 | 4-Cl | H | Me | Bu-t | OPr-i | |
| D-37 | 4-Cl | H | Me | Bu-t | Me | |
| D-38 | 4-Cl | H | Me | Bu-t | NH₂ | |
| D-39 | 4-Br | H | Me | Pr-i | OMe | 124–126 |
| D-40 | 4-Br | H | Me | Pr-i | OEt | 92–94 |
| D-41 | 4-Br | H | Me | Pr-i | OEt | 140–142 |
| D-42 | 4-Br | H | Me | Pr-i | NH₂ | 132–134 |
| D-43 | 4-Br | H | Me | Bu-s | OMe | |
| D-44 | 4-Me | H | Me | Pr-i | OMe | 76–77 |
| D-45 | 4-Me | H | Me | Pr-i | OEt | |
| D-46 | 4-Me | H | Me | Pr-i | OPr-i | |
| D-47 | 4-Me | H | Me | Pr-i | OCH₂Ph | |
| D-48 | 4-Me | Cl | Me | Pr-i | OMe | |
| D-49 | 4-Me | H | Me | Pr-i | OPen-cyc | |
| D-50 | 4-Me | H | Me | Pr-i | Me | |
| D-51 | 4-Me | H | Me | Pr-i | NH₂ | 140–146 |
| D-52 | 4-Me | H | Me | Pr-i | N(Me)₂ | |

TABLE 18-continued

| Compound No. | Xn | Y | R³ | R⁴ | R⁵ | Melting Point (°C.) |
|---|---|---|---|---|---|---|
| D-53 | 4-Me | H | Et | Et | OMe | |
| D-54 | 4-Me | H | Et | Et | OEt | |
| D-55 | 4-Me | H | Et | Et | OPr-i | |
| D-56 | 4-Me | H | Et | Et | Me | |

TABLE 19

| Compound No. | Xn | Y | R³ | R⁴ | R⁵ | Melting Point (°C.) |
|---|---|---|---|---|---|---|
| D-57 | 4-Me | H | Et | Et | NH₂ | |
| D-58 | 4-Me | H | Et | Et | N(Pr-n)₂ | |
| D-59 | 4-Br | H | Me | Bu-t | OMe | 127–128 |
| D-60 | 4-Br | H | Et | Et | OMe | |
| D-61 | 4-Br | H | Et | Et | OEt | |
| D-62 | 4-Br | H | Et | Et | OPr-i | |
| D-63 | 4-Et | H | Me | Pr-i | OMe | 82–83 |
| D-64 | 4-Et | H | Me | Pr-i | OMe | 101–102 |
| D-65 | 4-Et | H | Me | Pr-i | OMe | 96–98 |
| D-66 | 4-Pr-i | H | Me | Pr-i | OMe | |
| D-67 | 4-Pr-i | H | Me | Pr-i | Pr-i | |
| D-68 | 4-Pr-i | H | Me | Pr-i | NH₂ | |
| D-69 | 4-Pr-i | H | Et | Et | OMe | |
| D-70 | 4-Pr-i | H | Et | Et | OEt | |
| D-71 | 4-Pr-i | H | Et | Et | OPr-i | |
| D-72 | 4-Pr-i | H | Et | Et | NH₂ | |
| D-73 | 4-I | H | Me | Pr-i | OMe | 121–124 |
| D-74 | 4-I | H | Me | Pr-i | OEt | |
| D-75 | 4-I | H | Me | Pr-i | OPr-i | |
| D-76 | 4-I | H | Me | Bu-t | OMe | 132–134 |
| D-77 | 4-I | H | Et | Et | OMe | |
| D-78 | 4-Bu-t | H | Me | Pr-i | OMe | |
| D-79 | 4-Bu-t | H | Me | Pr-i | OEt | |
| D-80 | 4-Bu-t | H | Me | Pr-i | OPr-i | |
| D-81 | 4-Bu-t | H | Me | Pr-i | OCH₂CH=CH₂ | |
| D-82 | 4-Bu-t | H | Me | Pr-i | Me | |
| D-83 | 4-Bu-t | H | Me | Pr-i | NH₂ | |
| D-84 | 4-Bu-t | H | Me | Pr-i | N(Me)₂ | |
| D-85 | 4-Bu-t | H | Et | Et | OMe | |
| D-86 | 4-Bu-t | H | Et | Et | OPr-i | |

TABLE 20

| Compound No. | Xn | Y | R³ | R⁴ | R⁵ | Melting Point (°C.) |
|---|---|---|---|---|---|---|
| D-87 | 4-Bu-t | H | Et | Et | Me | |
| D-88 | 4-Bu-t | H | Et | Et | NH₂ | |
| D-89 | 4-CH=CHMe | H | Me | Pr-i | OMe | |
| D-90 | 4-C≡CMe | H | Me | Pr-i | OMe | |
| D-91 | 4-CF₃ | H | Me | Pr-i | OMe | 128–129 |
| D-92 | 4-CF₃ | H | Me | Pr-i | OMe | 159–160 |
| D-93 | 4-CF₃ | H | Me | Pr-i | OEt | 89–91 |
| D-94 | 4-CF₃ | H | Me | Pr-i | OPr-i | |
| D-95 | 4-CF₃ | H | Me | Pr-i | OCH₂CH=CH₂ | |
| D-96 | 4-CF₃ | H | Me | Pr-i | OCH₂C≡CH | |
| D-97 | 4-CF₃ | H | Me | Pr-i | Me | |
| D-98 | 4-CF₃ | H | Me | Pr-i | NH₂ | |
| D-99 | 4-CF₃ | H | Me | Pr-i | N(Me)₂ | 187–190 |
| D-100 | 4-CF₃ | H | Et | Et | OMe | |
| D-101 | 4-CF₃ | H | Et | Et | OEt | |
| D-102 | 4-CF₃ | H | Et | Et | OPr-i | |
| D-103 | 4-CF₃ | H | Et | Et | OCH₂Ph | |
| D-104 | 4-CF₃ | H | Me | Pr-i | OH | 136–139 |
| D-105 | 4-CF₃ | H | Me | Pr-i | NHMe | 150–152 |
| D-106 | 4-CF₃ | H | Et | Et | N(Me)₂ | |
| D-107 | 4-CF₃ | H | Me | Bu-t | OMe | |
| D-108 | 4-CF₃ | H | Me | Bu-t | OEt | |

TABLE 20-continued

| Compound No. | Xn | Y | $R^3$ | $R^4$ | $R^5$ | Melting Point (°C.) |
|---|---|---|---|---|---|---|
| D-109 | 4-$CF_3$ | H | Me | Bu-t | Me | |
| D-110 | 4-$CF_3$ | H | Me | Bu-t | NH | |
| D-111 | 4-OMe | H | Me | Pr-i | OMe | |
| D-112 | 4-OMe | H | Me | Pr-i | OEt | |
| D-113 | 4-OMe | H | Me | Pr-i | OPr-i | |
| D-114 | 4-OMe | H | Me | Pr-i | $NH_2$ | |
| D-115 | 4-OMe | H | Et | Et | OMe | |
| D-116 | 4-OMe | H | Et | Et | OEt | |

TABLE 21

| Compound No. | Xn | Y | $R^3$ | $R^4$ | $R^5$ | Melting Point (°C.) |
|---|---|---|---|---|---|---|
| D-117 | 4-OMe | H | Et | Et | OPr-i | |
| D-118 | 4-OMe | H | Et | Et | $NH_2$ | |
| D-119 | 4-$OCF_3$ | H | Me | Pr-i | OMe | 95–96 |
| D-120 | 4-$OCF_3$ | H | Me | Pr-i | OMe | 156–158 |
| D-121 | 4-OPr-i | H | Me | Pr-i | OMe | |
| D-122 | 4-OPr-i | H | Me | Pr-i | OEt | |
| D-123 | 4-OPr-i | H | Me | Pr-i | OPr-i | |
| D-124 | 4-OPr-i | H | Me | Pr-i | $NH_2$ | |
| D-125 | 4-OPr-i | H | Et | Et | OMe | |
| D-126 | 4-$OCF_3$ | H | Et | Et | OMe | |
| D-127 | 4-OPr-i | H | Et | Et | OPr-i | |
| D-128 | 4-OPr-i | H | Et | Et | $NH_2$ | |
| D-129 | 4-$OCHF_2$ | H | Me | Pr-i | OMe | |
| D-130 | 4-$OCHF_2$ | H | Me | Pr-i | $NH_2$ | |

TABLE 21-continued

| Compound No. | Xn | Y | $R^3$ | $R^4$ | $R^5$ | Melting Point (°C.) |
|---|---|---|---|---|---|---|
| D-131 | 4-Ph | H | Me | Pr-i | OMe | |
| D-132 | 4-Ph | H | Me | Pr-i | OEt | |
| D-133 | 4-Ph | H | Me | Pr-i | OPr-i | |
| D-134 | 4-Ph | H | Me | Pr-i | $NH_2$ | |
| D-135 | 4-SPh(2-Cl) | H | Et | Et | OMe | |
| D-136 | 4-S(O)Ph(2-Cl) | H | Et | Et | OMe | |
| D-137 | 4-$SO_2$Ph(2-Cl) | H | Et | Et | OMe | |
| D-138 | 4-SPh(3-$CF_3$) | H | Me | Bu-t | OMe | |
| D-139 | 4-S(O)Ph(3-$CF_3$) | H | Me | Bu-t | OMe | |
| D-140 | 4-$SO_2$Ph(3-$CF_3$) | H | Me | Bu-t | OMe | |
| D-141 | 4-SPh(4-Me) | H | Me | Pr-i | OMe | |
| D-142 | 4-S(O)Ph(4-Me) | H | Me | Pr-i | OMe | |
| D-143 | 4-$SO_2$Ph(4-Me) | H | Me | Pr-i | OMe | |
| D-144 | 4-$NO_2$ | H | Et | Et | OMe | |
| D-145 | 4-SMe | H | Me | Pr-i | OMe | |

TABLE 22

| Compound No. | Xn | Y | $R^3$ | $R^4$ | $R^5$ | Melting Point (°C.) |
|---|---|---|---|---|---|---|
| D-146 | 3,4-$Cl_2$ | H | Me | Pr-i | OMe | |
| D-147 | 3,4-$Cl_2$ | H | Me | Bu-t | OMe | |
| D-148 | 3,4-$Cl_2$ | H | Et | Et | OMe | |
| D-149 | 3,4-$Cl_2$ | H | Me | Bu-t | $NH_2$ | |

TABLE 23

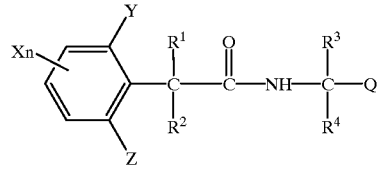

| Compound No. | Xn | Y | Z | $R^1$ | $R^2$ | $R^3$ | $R^4$ | Q | Melting Point (°C.) or Refractive Index ($n_D^{20}$) |
|---|---|---|---|---|---|---|---|---|---|
| E-1 | — | H | H | Me | Me | Et | Et | CN | |
| E-2 | — | H | H | Me | Me | Me | Pr-i | CN | |
| E-3 | — | H | H | Me | Me | Me | Bu-t | CN | |
| E-4 | 3-Me | H | H | Me | Me | Et | Et | CN | |
| E-5 | 3-Me | H | H | Me | Me | Me | Pr-i | CN | |
| E-6 | 3-Me | H | H | Me | Me | Me | Bu-t | CN | |
| E-7 | 4-Cl | H | H | Me | Me | Me | Me | CN | 105–106 |
| E-8 | 4-Cl | H | H | Me | Me | Me | Pr-i | CN | 87–89 |
| E-9 | 4-Cl | H | H | Me | Me | Me | Pr-cyc | CN | 93–94 |
| E-10 | 4-$CF_3$ | H | H | Me | Me | Et | Et | CN | |
| E-11 | 4-$CF_3$ | H | H | Me | Me | Me | Pr-i | CN | 107–108 |
| E-12 | 4-$CF_3$ | H | H | Me | Me | Me | Bu-t | CN | |
| E-13 | 4-Bu-t | H | H | Me | Me | Me | Et | CN | |
| E-14 | 4-Bu-t | H | H | Me | Me | Me | Pr-i | CN | |
| E-15 | 4-Bu-t | H | H | Me | Me | Me | Bu-t | CN | |
| E-16 | 4-Ph | H | H | Me | Me | Et | Et | CN | |
| E-17 | 4-Ph | H | H | Me | Me | Me | Pr-i | CN | |
| E-18 | 4-Me | H | H | Me | Me | Me | Pr-i | CN | 1.5116 |
| E-19 | 4-Cl | H | H | Me | Me | Et | Et | $CO_2Me$ | |
| E-20 | 4-Cl | H | H | Me | Me | Me | Pr-i | $CO_2Me$ | |
| E-21 | 4-Cl | Cl | H | Me | Me | Me | Pr-i | $CO_2Me$ | |
| E-22 | 4-$CF_3$ | H | H | Me | Me | Me | Pr-i | $CO_2Me$ | |
| E-23 | 4-$CF_3$ | H | H | Me | Me | Me | Bu-t | $CO_2Me$ | |

TABLE 23-continued

[Structure: Xn-phenyl (with Y and Z substituents) -C(R¹)(R²)-C(=O)-NH-C(R³)(R⁴)-Q]

| Compound No. | Xn | Y | Z | R¹ | R² | R³ | R⁴ | Q | Melting Point (°C.) or Refractive Index ($n_D^{20}$) |
|---|---|---|---|---|---|---|---|---|---|
| E-24 | — | H | H | H | Et | M6 | Pr-i | CN | |
| E-25 | — | H | H | H | Pr-cyc | Me | Pr-i | CN | |
| E-26 | — | H | H | H | Pr-i | Me | Pr-i | CN | |

TABLE 24

| Compound No. | Xn | Y | Z | R¹ | R² | R³ | R⁴ | Q | Melting Point (° C.) |
|---|---|---|---|---|---|---|---|---|---|
| E-27 | 3-Cl | H | H | H | Et | Me | Pr-i | CN | |
| E-28 | 3-Cl | H | H | H | Pr-cyc | Me | Pr-i | CN | |
| E-29 | 3-Cl | H | H | H | Pr-i | Me | Pr-i | CN | |
| E-30 | 4-Cl | H | H | H | Et | Me | Pr-i | CN | 120–122 |
| E-31 | 4-Cl | H | H | H | Et | Me | Pr-i | CN | 108–110 |
| E-32 | 4-Cl | H | H | H | Pr-i | Me | Pr-i | CN | 141–144 |
| E-33 | 4-Cl | H | H | H | Pr-i | Me | Pr-cyc | CN | 141–142 |
| E-34 | 4-Cl | H | H | H | Pr-i | Me | Me | CN | 143–145 |
| E-35 | 4-Cl | H | H | H | $CH_2F$ | Me | Pr-i | CN | |
| E-36 | 4-Cl | H | H | H | Et | Me | Pr-i | $CO_2Me$ | |
| E-37 | 4-CF | H | H | H | Et | Me | Pr-i | CN | 132–134 |
| E-38 | 4-$CF_3$ | H | H | H | Et | Me | Pr-i | CN | 109–111 |
| E-39 | 4-$CF_3$ | H | H | H | Pr-i | Me | Pr-i | CN | |
| E-40 | 4-$CF_3$ | H | H | H | $CH_2F$ | Me | Pr-i | CN | |
| E-41 | 4-$CF_3$ | H | H | H | Et | Me | Pr-i | $CO_2Me$ | |
| E-42 | 4-Bu-t | H | H | H | Et | Me | Pr-i | CN | |
| E-43 | 4-Bu-t | H | H | H | Pr-cyc | Me | Pr-i | CN | |
| E-44 | 4-Bu-t | H | H | H | Pr-i | Me | Pr-i | CN | |
| E-45 | 4-Bu-t | H | H | H | $CH_2F$ | Me | Pr-i | CN | |
| E-46 | 4-Bu-t | H | H | H | Et | Me | Pr-i | $CO_2Me$ | |
| E-47 | 4-Me | H | H | Pr-n | Pr-n | Me | Pr-i | CN | |
| E-48 | 4-Me | H | H | H | Pr-cyc | Me | Pr-i | CN | |
| E-49 | 4-Me | H | H | H | Pr-i | Me | Pr-i | CN | |
| E-50 | 4-Me | H | H | H | $CF_3$ | Me | Pr-i | CN | |
| E-51 | 4-Me | H | H | H | Et | Me | Pr-i | $CO_2Me$ | |
| E-52 | 4-Cl | F | F | H | Me | Me | Pr-i | CN | |
| E-53 | 4-Cl | Cl | Cl | H | Me | Me | Pr-i | CN | |
| E-54 | 4-OMe | H | H | H | $CHF_2$ | Me | Pr-i | CN | |

Compound Nos. C-42, C-43, C-196, C-197, C-198, and C-199 are optically active compounds, and having angles of rotation of $[\alpha]D^{22}=+32.7°$ (c=0.5, $CHCl_3$), $[\alpha]D^{22}=-27.3°$ (c=0.5, $CHCl_3$), $[\alpha]D^{22}=+9.8°$ (c=1.0, $CHCl_3$), $[\alpha]D^{22}=+23.4°$ (c=1.0, $CHCl_3$), $[\alpha]D^{22}=-8.4°$ (c=1.0, $CHCl_3$), and $[\alpha]D^{22}=-19.9°$ (c=1.0, $CHCl_3$), respectively.

Compound Nos. C-16, C-17, C-18, C-21, C-24, C-27, C-34, C-39, C-47, C-51, C-54, C-62, C-66, C-71, C-73, C-75, C-81, C-88, C-92, C-94, C-99, C-102, C-106, C-108, C-112, C-114, C-117, C-122, C-129, C-131, C-140, C-157, C-161, C-165, C169, C-171, C-174, C-177, C-179, C-181, C-184, C-187, C-189, C-193, C-196, C-198, C-200, D-40, D-63, D-91, D-119, E-30, and E-37 are A-configurational diastereomers. Compound Nos. C-19, C-22, C-25, C-28, C-35, C-40, C-48, C-52, C-55, C-63, C-67, C-72, C-74, C-76, C-82, C-89, C-93, C-95, C-100, C-103, C-107, C-109, C-113, C-115, C-118, C-123, C-130, C-141, C-158, C-162, C-166, C-170, C-172, C-175, C-178, C-180, C-182, C-185, C-188, C-190, C-194, C-197, C-199, C-201, D-41, D-64, D-92, D-120, E-31, and E-38 are B-configurational diastereomers. In addition, the other compounds having two or more of asymmetric carbon atoms are diastereomer mixtures.

"A-configurational diastereomer" means a low-polar diastereomer separated by a column chromatography on silica gel, a high performance liquid chromatography, or the like, while "B-configurational diastereomer" means a high-polar diastereomer separated in the same manner as mentioned above.

The compounds represented by Formula (1) can be synthesized according to, for example, the preparation processes shown below.

Preparation Process 1

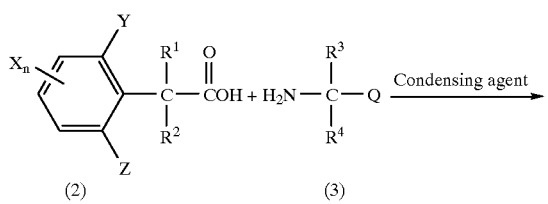

(wherein $R^1$, $R^2$, $R^3$, $R^4$, X, Y, Z, Q, and n have the same meanings as defined above).

The compounds of Formula (1) according to the present invention may be prepared by the reaction of phenylalkanoic acid derivatives represented by Formula (2) and amines represented by Formula (3) using a condensing agent, in the presence of a catalyst and/or a base, if necessary.

The present reaction can be carried out in a solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as methylene chloride, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitrites such as acetonitrile, propionitrile, and the like, aprotic polar solvents such as dimethylsulfoxide, N,N-dimethylformamide, sulfolane, and the like, and mixture of solvents combining solvents selected from the aforementioned.

As the condensing agent, there can be mentioned 1-ethyl-3-(3-dimethylaminopropyl)carbodiimide hydrochloride, N,N'-dicyclohexylcarbodiimide, carbonyldiimidazol, 2-chloro-1,3-dimethylimidazolium chloride, or the like.

As the catalyst, there can be mentioned, for example, 4-dimethylaminopyridine, 1-hydroxybenzotriazole, dimethylformamide or the like.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, organic bases such as triethylamine, trimethylamine, N,N-dimethylaniline, pyridine, N-methylpiperidine, 1,5-diazabicyclo[4.3.0]non-5-ene (DBN), 1,8-diazabicyclo[5.4.0]undec-7-ene (DBU), and the like, and amines such as triethylamine, pyridine, N-methylpiperidine and the like.

The present reaction is carried out at a temperature of −50° C. to 150° C., and preferably 0° C. to 60° C. The reaction time is preferably in the range from 1 to 30 hours.

Next, the synthesis process for each starting material will be explained.

The compounds represented by Formula (2) can be synthesized, for example, by hydrolyzing phenylmalonates by means of an alkaline, heating the hydrolyzed product, and subsequently decarbonating the heated product. This preparation process has been disclosed in the Journal of Organic Chemistry, Vol. 13, p. 763 (1948); Organic Syntheses, Vol 3, p. 557, 1955; Japanese Patent Application First Publication, No. Sho 40-7491; and Synthesis, Vol. 6, p. 456, 1982.

In addition, the compounds represented by Formula (3) can be synthesized, for example, using a ketone, sodium cyanide, and ammonium chloride, according to Strecker Method, which has been disclosed in Organic Syntheses, Vol. 3, p. 88, 1955; Journal of Medicinal Chemistry, Vol. 9, p. 911, 1966; or Tetrahedron Letters, Vol. 17, p. 1455, 1977.

Preparation Process 2

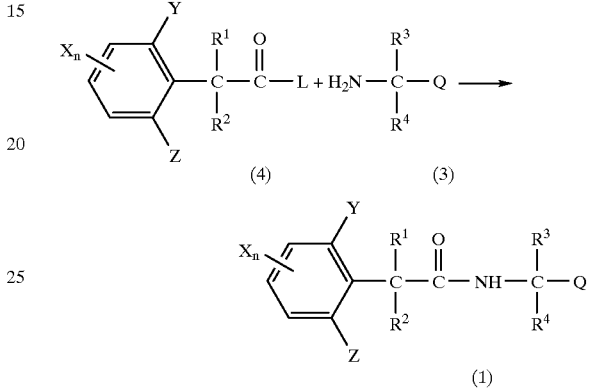

(wherein $R^1$, $R^2$, $R^3$, $R^4$, X, Y, Z, Q, and n have the same meanings as defined above, and L represents a halogen atom).

The compounds represented by Formula (1) according to the present invention may be prepared by the reaction of phenylalkanoic acid halides represented by Formula (4) and amines represented by Formula (3).

The present reaction can be carried out in a solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as methylene chloride, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitrites such as acetonitrile, propionitrile, and the like, aprotic polar solvents such as N,N-dimethylformamide, sulfolane, and the like, and mixture of solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, organic bases such as triethylamine, trimethylamine, N,N-dimethylaniline, pyridine, N-methylpiperidine, 1,5-diazabicyclo[4.3.0]non-5-ene (DBN), 1,8-diazabicyclo[5.4.0]undec-7-ene (DBU), and the like, and more preferably a tertiary amine such as triethylamine, pyridine, N-methylpiperidine, or the like.

The present reaction is carried out at a temperature of −50° C. to 150° C., and preferably 0° C. to 60° C. The reaction time is preferably in the range from 1 to 30 hours.

Next, the preparation process for the starting material employed in the present preparation process will be explained.

The phenylalkanoic acid halides represented by Formula (4) can be prepared by the reaction of the phenylalkanoic acids represented by Formula (2) prepared by the above-mentioned method, for example, and halogenating agents such as thionyl chloride, phosphorus pentachloride, phosphorus tribromide, or the like.

Preparation Process 3

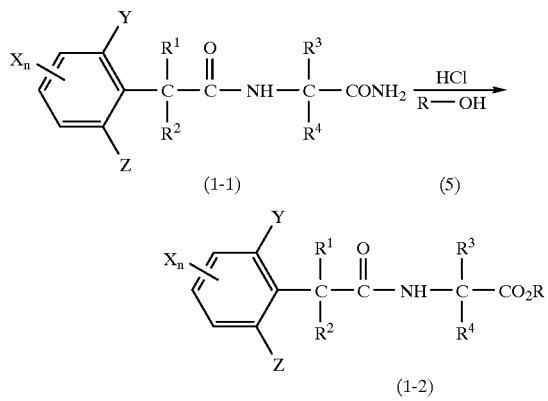

(wherein $R^1$, $R^2$, $R^3$, $R^4$, X, Y, Z, and n have the same meanings as defined above, and R represents a $C_1$–$C_6$ alkyl group).

The compounds represented by Formula (1-2) according to the present invention may be prepared by the reaction of the compounds represented by Formula (1-1) according to the present invention and alcohols represented by Formula (5) which is saturated with hydrogen chloride.

The present reaction can be carried out in a solvent: this solvent can be any solvent that does not hinder the reaction, for example, alcohols such as methanol, ethanol, propanol, isopropanol, butanol, and the like, hydrocarbons such as pentane, hexane, heptane, cyclohexane, petroleum ether, ligroin, benzene, toluene, xylene and the like, halogenated hydrocarbons such as methylene chloride, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, and mixture of solvents combining solvents selected from the aforementioned.

The present reaction is carried out at a temperature of −50° C. to 150° C., and preferably 0° C. to 120° C. The reaction time is preferably in the range from 1 to 20 hours.

BEST MODES FOR CARRYING OUT THE PRESENT INVENTION

In the following, preparation examples of the compounds according to the present invention are provided.

Preparation Example 1

Synthesis of N-(1-Cyano-1,2-dimethylpropyl)-2-(4-biphenylyl)acetamide (Compound No. A-87)

1.1 g (5.7 mmol) of 1-ethyl-3-(3-dimethylaminopropyl) carbodiimide hydrochloride was added to a solution containing 1.0 g (4.5 mmol) of 4-biphenylylacetic acid dissolved in 50 ml of methylene chloride at room temperature, and the mixture was stirred for 10 min. Subsequently, 0.5 g (4.7 mmol) of 2-amino-2,3-dimethylbutyronitrile was added dropwise, and the whole mixture was stirred for 3 hours at room temperature. After completion of the reaction, water was added to the resulting mixture and the methylene chloride layer was washed with water, and subsequently dried over anhydrous magnesium sulfate. The methylene chloride was removed from the organic layer under reduced pressure. The residue was purified by column chromatography on silica gel, thus yielding 1.1 g (yield: 76%) of the desired compound having a melting point of 151° C.–152° C.

Preparation Example 2

Synthesis of N-(1-Cyano-1,2-dimethylpropyl)-2-(4-bromophenyl)propionamide (Compound Nos. C-47 and C-48)

0.9 g (8.0 mmol) of 2-amino-2,3-dimethylbutyronitrile and 0.8 g (7.9 mmol) of triethylamine were dissolved in 20 ml of tetrahydrofuran. 1.5 g (6.0 mmol) of 2-(4-bromophenyl)propionyl chloride was added to the mixture which was being stirred at 10° C., in dropwise manner over 5 minutes. After completion of the dropping, the reaction mixture was stirred for 5 hours at room temperature. The reaction mixture was concentrated, and subsequently water was added thereto. The organic layer was extracted with ethyl acetate and then was dried over anhydrous magnesium sulfate. The ethyl acetate was removed from the organic layer under reduced pressure. The residue was purified by column chromatography on silica gel, thus yielding 0.45 g (yield: 24%) of the A-configurational diastereomer (low polar product) having a melting point of 130° C.–131° C., and 0.75 g (yield: 40%) of the B-configurational diastereomer (high polar product) having a melting point of 121° C.–123° C.

Preparation Example 3

Synthesis of N-(1-Carbamoyl-1-ethylpropyl)-2-(4-chlorophenyl)propionamide (Compound No. D-32)

2.3 g (18 mmol) of 2-amino-2-ethylbutylamide and 2.0 g (20 mmol) of triethylamine were suspended in 50 ml of tetrahydrofuran. A tetrahydrofuran solution (10 ml) containing 3.0 g (15 mmol) of 2-(4-chlorophenyl)propionyl chloride dissolved therein was added dropwise to the suspension which was being stirred at room temperature, over 10 minutes. After completion of the dropping, the reaction mixture was stirred for 3 hours at room temperature. The reaction mixture was concentrated, and subsequently water was added thereto. The organic layer was extracted with chloroform and then was dried over anhydrous magnesium sulfate. The chloroform was removed from the organic layer under reduced pressure. The obtained crystal was washed with diisopropyl ether, thus yielding 4.2 g (yield: 95%) of the desired product having a melting point of 116° C.–118° C.

Preparation Example 4

Synthesis of Methyl 2-[1-(4-chlorophenyl) ethylcarbonylamino]-2-ethylbutyrate (Compound No. D-28)

0.6 g (2.0 mmol) of N-(1-carbamoyl-1-ethylpropyl)-2-(4-chlorophenyl)propionamide was dissolved in 10 ml of hydrogen chloride-saturated methanol. The solution was refluxed for 3 hours. The reaction mixture was concentrated, and subsequently water was added thereto. The organic layer was extracted with ethyl acetate and then was dried over anhydrous magnesium sulfate. The ethyl acetate was removed from the organic layer under reduced pressure. The residue was purified by column chromatography on silica gel, thus yielding 0.5 g (yield: 81%) of the desired product having a melting point of 98° C.–99° C.

Preparation Example 5

Synthesis of N-(1-Cyano-1-cyclopropylethyl)-2-(4-chlorophenyl)-2-methylpropionamide (Compound No. E-9)

0.25 g (2.3 mmol) of 2-amino-2-cyclopropylpropiononitrile and 0.3 g (3.0 mmol) of triethylamine were dissolved in 20 ml of tetrahydrofuran. 0.5 g (2.3 mmol) of 2-(4-chlorophenyl)-2-methylpropionyl chloride was added to the mixture which was being stirred at 10° C., in dropwise manner over 5 minutes. After completion of the dropping, the reaction mixture was stirred for 3 hours at room temperature. The reaction mixture was concentrated, and subsequently water was added thereto. The organic layer was extracted with ethyl acetate and then was dried over anhydrous magnesium sulfate. The ethyl acetate was removed from the organic layer under reduced pressure. The residue was purified by column chromatography on silica gel, thus yielding 0.5 g (yield: 75%) of the desired product having a melting point of 93° C.–94° C.

Preparation Example 6

Synthesis of Isopropyl 2-(4-trifluoromethylbenzylcarbonylamino)-2,3-dimethylbutyrate (Compound No. B-36)

1.1 g (5.7 mmol) of 1-ethyl-3-(3-dimethylaminopropyl) carbodiimide hydrochloride was added to a solution containing 1.0 g (4.9 mmol) of 4-trifluoromethylphenylacetic acid dissolved in 50 ml of methylene chloride at room temperature, and then the mixture was stirred for 10 minutes. 0.9 g (5.2 mmol) of isopropyl 2-amino-2,3-dimethylbutyrate was added thereto and the entire mixture was stirred for 3 hours at room temperature. After completion of the reaction, water was added to the reaction mixture. The methylene chloride layer was washed with water and then dried over anhydrous magnesium sulfate. The methylene chloride was removed under reduced pressure. The residue was purified by column chromatography on silica gel, thus yielding 1.4 g (yield: 80%) of the desired product having a melting point of 122° C.–123° C.

The agricultural or horticultural fungicides according to the present invention include phenylalkane amide derivatives represented by Formula (1) as active ingredients. In the case where the compounds according to the present invention are employed as an agricultural or horticultural fungicides, the compounds acting as the active ingredients can be formulated appropriately, depending on the purpose. The active ingredient is usually diluted in an inert liquid or a solid carrier, and a surfactant and the like are added thereto, if necessary. The mixture is then formulated in a known manner into, for example, a fine powder, a wettable powder, an emulsifiable concentrate, granules, or the like.

As the suitable carriers employed in the formulation, there can be mentioned solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like. As the surfactants and dispersants, there can be mentioned dinaphthylmethane disulfonate, alcohol sulfates, alkyl aryl sulfonates, ligninsulfonates, polyoxyethylene glycol ethers, polyoxyethylene alkyl aryl ethers, polyoxyethylenesorbitan monoalkylates, and the like. As the auxiliary agents, there can be mentioned carboxymethyl cellulose, and the like. The formulated agricultural or horticultural fungicide according to the present invention can be spread in an appropriate diluted concentration or can be applied directly.

The agricultural or horticultural fungicide according to the present invention can be employed for spraying the stem and leaf portions, applying to the soil, and submerged application. The proportion of the active ingredient is selected as needed. When formulated into a fine powder or granules, 0.1% by weight to 20% by weight of the active ingredient are preferred. For an emulsifiable concentrate or wettable powder, 5% by weight to 80% by weight of the active ingredient are preferred.

The rate of application of the agricultural or horticultural fungicide according to the present invention may vary depending on the kind of the compounds, the kind of the pest or disease to be controlled, the nature of occurrence of the pest or disease, the degree of damage, environmental conditions, the form of preparation to be used, and the like. When the agricultural or horticultural fungicide of the present invention is applied directly in the form of fine powder or granules, it is recommended that the rate of application of the active ingredient be suitably chosen within the range of 0.1 g to 5 kg per 10 ares, and preferably, in the range of 1 g to 1 kg per 10 ares. In addition, when the fungicide of the present invention is in the form of a liquid such as an emulsifiable concentrate or a wettable powder, it is recommended that the ratio for application of the active ingredient be suitably chosen within the range of 0.1 ppm to 10,000 ppm, and preferably within the range of 10 ppm to 3,000 ppm.

The agricultural or horticultural fungicide of the present invention can control plant diseases caused by the pathogenic fungi in the Oomycetes, Ascomycetes, Deuteromycetes, Oomycetes, and Basidiomycetes in the formulation mentioned above.

In the following, the examples of the fungi, but not limited to, will be listed: Pyricularia such as rice blast fungi (*Pyricularia oryzae*), Sphaerotheca such as cucumber powdery mildew fungi (*Sphaerotheca fuliginea*), Venturia such as apple scab fungi (*Venturia inaequalis*), Gibberella such as "Bakanae" disease fungi (*Gibberella fujikuroi*), Botrytis such as cucumber gray mold fungi (*Botrytis cinerea*), Alternaria such as chinese mustard sooty spot fungi (*Alternaria brassicicola*), Rhizoctonia such as rice sheath blight fungi (*Rhizoctonia solani*), Puccinia such as rust fungi (*Puccinia recondita*), Pseudoperonospora such as cucumber downey mildew fungi (*Pseudoperonospora cubensis*).

In addition, the compound according to the present invention may be employed alone or in combination with other fungicides, insecticides, herbicides, plant growth modifiers, fertilizers or the like. Next, the representative formulations are illustrated with reference to the following Formulation Examples, wherein all "%" represent "percent by weight".

Formulation Example 1

Fine Powder

2% of Compound No. A-4, 5% of diatomaceous earth, and 93% of clay were uniformly mixed and ground into a fine powder.

Formulation Example 2

Wettable Powder

50% of Compound No. B-6, 45% of diatomaceous earth, 2% of sodium dinaphthylmethane disulfonate, and 3% of sodium ligninsulfonate were uniformly mixed and ground into a wettable powder.

Formulation Example 3

Emulsifiable Concentrate

30% of Compound No. C-29, 20% of cyclohexanone, 11% of polyoxyethylene alkyl aryl ether, 4% of calcium alkylbenzenesulfonate, and 35% of methylnaphthalene were uniformly dissolved, thus yielding an emulsifiable concentrate.

Formulation Example 4

Granules

5% of Compound No. B-34, 2% of sodium salt of lauryl alcohol sulfate, 5% of sodium ligninsulfonate, 2% of carboxymethyl cellulose, and 86% of clay were mixed and ground. 20 parts by weight of water was added to 100 parts by weight of the ground mixture. The resulting mixture was kneaded and formed into granules of 14 mesh to 32 mesh by means of an extrusion granulator, and then dried into the desired granules.

In the following, the effects which the agricultural or horticultural fungicides according to the present invention exhibit will be explained by reference to Test Examples. In Test Examples, the compound disclosed in Japanese Patent Application, First Publication, No. Hei 6-220004 was employed as a comparative compound.

Test Example 1

Test on the Preventive Effects for Rice Blast (*Pyricularia oryzae*)

Rice seeds (variety: Aichi Asahi) were sown at a rate of approximately 15 grains each in porcelain pots having a diameter of 7 cm. The seeds were allowed to germinate and grow for 3–4 weeks in a greenhouse. A wettable powder prepared according to Formulation Example 2 was diluted with water to a concentration of 500 ppm of the active ingredient, and subsequently the obtained aqueous preparation was sprayed at a rate of 10 ml per pot to the rice seedlings at their 4 leaf stage. After dried in the air, the seedlings were inoculated with a conidiospore suspension of rice blast fungi (*Pyricularia oryzae*) and immediately placed in a moist chamber at 25° C. for 24 hours and subsequently in a greenhouse. On the fifth day after the inoculation, the number of lesions on the fourth leaf was countered. The controlling activity was calculated according to Equation 1. The evaluation results obtained according to the Evaluation Standard shown in Table 25 are shown in Tables 26–28.

$$\text{Controlling Activity (\%)} = \left(1 - \frac{\text{the Number of Lesions in Treated Plot}}{\text{the number of Lesions in Untreated Plot}}\right) \times 100 \quad \text{Equation 1}$$

TABLE 25

| Evaluation | Controlling Activity |
|---|---|
| A | 100% |
| B | 80% or more and less than 100% |
| C | 50% or more and less than 80% |
| D | less than 50% |

TABLE 26

| Compound No. | Evaluation |
|---|---|
| A-2 | A |
| A-4 | A |
| A-6 | A |
| A-8 | A |
| A-9 | B |
| A-10 | A |
| A-15 | A |
| A-19 | B |

TABLE 26-continued

| Compound No. | Evaluation |
|---|---|
| A-20 | A |
| A-23 | A |
| A-26 | A |
| A-30 | A |
| A-31 | A |
| A-33 | A |
| A-34 | A |
| A-35 | A |
| A-41 | A |
| A-52 | A |
| A-54 | A |
| A-56 | A |
| A-57 | A |
| A-60 | A |
| A-61 | A |
| A-62 | A |
| A-63 | A |
| A-64 | A |
| A-68 | A |
| A-71 | B |
| A-74 | B |
| A-75 | B |
| A-76 | A |
| A-78 | B |
| A-81 | A |
| A-82 | B |
| A-86 | A |
| A-87 | A |
| A-92 | A |
| A-104 | A |
| A-105 | A |
| A-107 | A |
| A-117 | B |
| B-6 | A |
| B-7 | A |
| B-8 | A |
| B-13 | B |
| B-34 | A |
| B-35 | A |
| B-36 | A |
| B-41 | B |
| B-116 | A |
| B-140 | A |
| C-1 | B |
| C-2 | B |
| C-3 | A |
| C-13 | A |
| C-16 | A |
| C-17 | A |
| C-18 | A |
| C-19 | A |
| C-21 | B |
| C-22 | B |
| C-24 | A |
| C-25 | A |
| C-27 | A |
| C-28 | A |
| C-29 | A |
| C-30 | A |
| C-32 | A |
| C-33 | A |
| C-34 | A |

TABLE 27

| Compound No. | Evaluation |
|---|---|
| C-35 | A |
| C-38 | A |
| C-39 | A |
| C-40 | A |
| C-41 | A |
| C-42 | A |
| C-43 | A |

TABLE 27-continued

| Compound No. | Evaluation |
| --- | --- |
| C-47 | A |
| C-48 | A |
| C-49 | A |
| C-51 | A |
| C-52 | A |
| C-53 | A |
| C-54 | A |
| C-55 | A |
| C-56 | A |
| C-62 | A |
| C-63 | A |
| C-64 | A |
| C-71 | A |
| C-72 | A |
| C-73 | A |
| C-74 | A |
| C-75 | A |
| C-76 | B |
| C-81 | A |
| C-82 | A |
| C-87 | A |
| C-88 | A |
| C-89 | B |
| C-94 | A |
| C-95 | A |
| C-99 | A |
| C-100 | A |
| C-101 | A |
| C-106 | A |
| C-107 | B |
| C-108 | A |
| C-109 | A |
| C-112 | A |
| C-113 | B |
| C-120 | A |
| C-121 | A |
| C-122 | A |
| C-123 | A |
| C-125 | A |
| C-129 | A |
| C-130 | A |
| C-131 | A |
| C-137 | A |
| C-140 | A |
| C-141 | B |
| C-157 | A |
| C-158 | A |
| C-159 | A |
| C-161 | A |
| C-162 | A |
| C-165 | A |
| C-166 | A |
| C-169 | A |
| C-170 | B |
| C-171 | A |
| C-172 | A |
| C-173 | A |
| C-174 | A |
| C-175 | A |
| C-176 | A |
| C-177 | A |
| C-178 | A |
| C-179 | A |

TABLE 28

| Compound No. | Evaluation |
| --- | --- |
| C-180 | B |
| C-181 | A |
| C-182 | A |
| C-184 | B |
| C-185 | B |
| C-186 | B |
| C-187 | A |
| C-188 | B |
| C-189 | A |
| C-190 | A |
| C-191 | A |
| C-192 | B |
| C-193 | B |
| C-194 | B |
| C-195 | B |
| C-196 | A |
| C-197 | A |
| C-198 | A |
| C-199 | A |
| C-200 | B |
| C-201 | B |
| C-202 | B |
| D-19 | A |
| D-20 | A |
| D-21 | A |
| D-26 | A |
| D-28 | A |
| D-29 | A |
| D-32 | A |
| D-34 | B |
| D-39 | A |
| D-40 | A |
| D-41 | A |
| D-42 | A |
| D-59 | B |
| D-63 | B |
| D-64 | A |
| D-65 | B |
| D-73 | A |
| D-76 | B |
| D-91 | A |
| D-92 | A |
| D-99 | B |
| D-104 | B |
| D-105 | B |
| D-119 | A |
| D-120 | B |
| E-7 | B |
| E-8 | B |
| E-9 | A |
| E-11 | B |
| E-18 | A |
| E-32 | B |
| E-33 | A |
| E-34 | A |
| E-37 | B |
| E-38 | B |

Test Example 2

Test on the Submerged Application Effects for Rice Blast (*Pyricularia oryzae*)

Rice seedlings (variety: Aichi Asahi) at their 2-leaf stage were transplanted at 4 spots at a rate of 3 seedlings per location each in white porcelin locations having a diameter of 9 cm. The seedlings were allowed to germinate and grow in a greenhouse. When the seedlings grew to the 3-leaf stage, granules prepared according to Formulation Example 4 were applied into the irrigation water in the pot so that the concentration of the active ingredient was at 300 g per 10 ares. When the fourth leaf was completely developed, the seedlings were inoculated with a spore suspension of rice blast fungi (*Pyricularia oryzae*) and immediately placed in a moist chamber at 25° C. for 24 hours and subsequently in a greenhouse so as to induce an attack of the disease. On the fifth day after the inoculation, the number of lesions on the fourth leaf was countered. The controlling activity was calculated according to Equation 1. The evaluation results obtained according to the Evaluation Standard shown in Table 25 are shown in Table 29.

TABLE 29

| Compound No. | Evaluation |
|---|---|
| A-4 | A |
| A-6 | A |
| A-15 | A |
| A-19 | A |
| A-20 | A |
| A-23 | A |
| A-26 | B |
| A-41 | A |
| A-52 | A |
| A-54 | A |
| A-56 | A |
| A-71 | A |
| A-76 | A |
| A-117 | B |
| B-6 | A |
| B-13 | A |
| B-34 | A |
| C-1 | A |
| C-2 | A |
| C-3 | A |
| C-13 | A |
| C-16 | B |
| C-17 | B |
| C-21 | B |
| C-29 | A |
| C-33 | A |
| C-39 | A |
| C-40 | A |
| C-41 | A |
| C-49 | A |
| C-56 | A |
| C-62 | A |
| C-64 | A |
| C-94 | A |
| C-169 | A |
| C-170 | A |
| C-171 | A |
| C-172 | A |
| C-176 | A |
| C-177 | A |
| C-178 | A |
| C-187 | A |
| C-189 | B |
| C-192 | B |
| C-196 | A |
| C-197 | B |
| C-198 | B |
| C-199 | B |
| C-95 | B |
| D-76 | B |
| E-7 | A |
| E-18 | A |
| Comparative compound | D |

Example 3

Test on the Preventive Effects for Scab (*Venturia inaequalis*)

Apple seeds (variety: Jonathan) were sown at a rate of 4 grains each in plastic pots having a diameter of 5.5 cm. A wettable powder prepared according to Formulation Example 2 was diluted with water to a concentration of 50 ppm of the active ingredient, and subsequently the obtained aqueous preparation was sprayed at a rate of 20 ml per pot to the apple seedlings in which the fourth true leaf was completely developed. After dried in the air, the seedlings were inoculated with a spore suspension of apple scab fungi (*Venturia inaequalis*) and immediately placed in a moist chamber at 20° C. for 48 hours and subsequently in a greenhouse. On the fourteenth day after the inoculation, the infected area on the leaves was searched. The incidence index was evaluated according to the Evaluation Standard shown in Table 30. Using the incidence index and the number of the infected leaves, degree of damage was calculated according to Equation 2, and the controlling activity was calculated according to Equation 3. The obtained controlling activity was evaluated according to the Evaluation Standard shown in Table 25, and the results are shown in Table 31.

TABLE 30

| Incidence Index | Infected Area |
|---|---|
| 0 | No lesions |
| 1 | Less than 5% |
| 2 | 5% or more and less than 33.3% |
| 3 | 33.3% or more and less than 66.6% |
| 4 | 66.6% or more |

Equation (2):

$$\text{Degree of Damage (\%)} = \frac{\sum(\text{Incidence Index} \times \text{Number of Infected Leaves})}{4 \times \text{Number of Leaves Examined}} \times 100$$

Equation (3):

$$\text{Controlling Activity (\%)} = \left(1 - \frac{\text{Degree of Damage in Treated Plot}}{\text{Degree of Damage In Untreated Plot}}\right) \times 100$$

TABLE 31

| Compound No. | Evaluation |
|---|---|
| A-20 | A |
| A-26 | B |
| A-62 | A |
| A-63 | A |
| A-64 | A |
| A-76 | B |
| A-104 | A |
| A-105 | A |
| A-117 | B |
| B-6 | A |
| C-18 | A |
| C-54 | A |
| C-55 | A |
| C-73 | A |
| C-75 | A |
| C-140 | A |
| C-141 | A |
| C-174 | B |
| C-175 | B |
| C-177 | A |
| C-178 | A |
| C-196 | B |
| C-198 | B |
| C-200 | B |
| C-201 | B |
| C-202 | A |
| D-76 | A |

TABLE 31-continued

| Compound No. | Evaluation |
| --- | --- |
| D-91 | A |
| D-92 | A |
| Comparative compound | D |

What is claimed is:

1. A phenylalkane amide derivative represented by Formula (1):

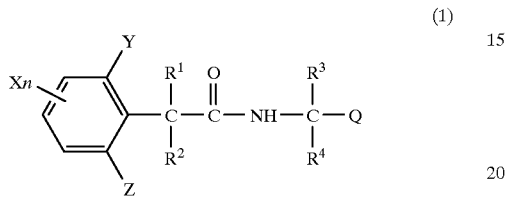

(1)

wherein $R^1$ represents a hydrogen atom or a $C_1$–$C_6$ alkyl group, $R^2$ represents a hydrogen atom, a $C_1$–$C_6$ alkyl group, a $C_3$–$C_6$ cycloalkyl group, or a $C_1$–$C_4$ haloalkyl group, $R^3$ and $R^4$ each independently represents a $C_1$–$C_6$ alkyl group, a $C_2$–$C_6$ alkenyl group, a $C_3$–$C_6$ cycloalkyl group, a $C_2$–$C_6$ alkoxyalkyl group, or a $C_1$–$C_4$ haloalkyl group, or $R^3$ and $R^4$, together with the carbon atom to which they are bonded, form a cycloalkyl group of 5-membered to 7-membered ring (which may be substituted by a $C_1$–$C_6$ alkyl group), Q represents a cyano group or a group of the formula: —$COR^5$ (wherein $R^5$ represents a hydroxy group, a $C_1$–$C_6$ alkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a phenoxy group, a benzyloxy group, an amino group, a $C_1$–$C_6$ alkylamino group, or a $C_1$–$C_6$ dialkylamino group), X represents a halogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a hydroxy group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, an aryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylthio group, a $C_1$–$C_6$ alkylsulfinyl group, a $C_1$–$C_6$ alkylsulfonyl group, a $C_1$–$C_4$ haloalkylthio group, an arylthio group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroarylthio group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an arylsulfinyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an arylsulfonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an amino group, a $C_1$–$C_6$ alkylamino group, a $C_1$–$C_6$ dialkylamino group, a nitro group, a cyano group, or an aryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), an aralkyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylcarbonyl group, an arylcarbonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroarylcarbonyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a formyl group, or a $C_1$–$C_6$ alkoxycarbonyl group, Y and Z each independently represents a hydrogen atom, a $C_1$–$C_6$ alkyl group, a $C_1$–$C_4$ haloalkyl group, a $C_1$–$C_6$ alkoxy group, a cyano group, a nitro group, or a halogen atom, and n represents an integer of 0–3, with the exception that $R^3$ and $R^4$ represent a trifluoromethyl group at the same time, and with the proviso that when both $R^1$ and $R^2$ represent a hydrogen atoms at the same time, both Y and Z represent a hydrogen atom and n represents an integer of 1–3.

2. A phenylalkane amide derivative represented by Formula (1):

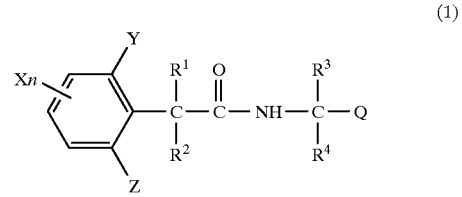

(1)

wherein $R^1$ represents a hydrogen atom or a $C_1$–$C_6$ alkyl group, $R^2$ represents a hydrogen atom, a $C_1$–$C_6$ alkyl group, a $C_3$–$C_6$ cycloalkyl group, or a $C_1$–$C_4$ haloalkyl group, $R^3$ and $R^4$ each independently represents a $C_1$–$C_6$ alkyl group, a $C_2$–$C_6$ alkenyl group, a $C_3$–$C_6$ cycloalkyl group, or a $C_1$–$C_4$ haloalkyl group, or $R^3$ and $R^4$, together with the carbon atom to which they are bonded, form a cycloalkyl group of 5-membered to 7-membered ring (which may be substituted by a $C_1$–$C_6$ alkyl group), Q represents a cyano group or a group of a formula: —$COR^5$ (wherein $R^5$ represents a hydroxy group, a $C_1$–$C_6$ alkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a phenoxy group, a benzyloxy group, an amino group, a $C_1$–$C_6$ alkylamino group, or a $C_1$–$C_6$ dialkylamino group), X represents a halogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a hydroxy group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, a $C_1$–$C_4$ haloalkylthio group, an aryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylthio group, a $C_1$–$C_6$ alkylamino group, a $C_1$–$C_6$ dialkylamino group, a nitro group, a cyano group, an aryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryl group, an aralkyl group, a $C_1$–$C_6$ alkylcarbonyl group, a formyl group, an arylcarbonyl group, a heteroarylcarbonyl group, or a $C_1$–$C_6$ alkoxycarbonyl group, Y and Z each independently represents a hydrogen atom, a $C_1$–$C_6$ alkyl group, a $C_1$–$C_4$ haloalkyl group, a $C_1$–$C_6$ alkoxy group, a cyano group, a nitro group, or a halogen atom, and n represents an integer of 0–3, with the exception that $R^3$ and $R^4$ represent a trifluoromethyl group at the same time, and with the proviso that when both $R^1$ and $R^2$ represent a hydrogen atom at the same time, both Y and Z represent a hydrogen atom and n represents an integer of 1–3.

3. A phenylalkane amide derivative represented by Formula (1):

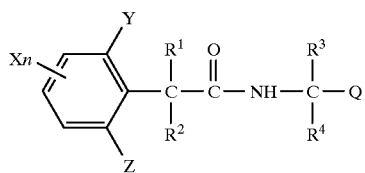

(1)

wherein $R^1$ represents a hydrogen atom or a $C_1$–$C_6$ alkyl group, $R^2$ represents a hydrogen atom, or a $C_1$–$C_6$ alkyl group, $R^3$ and $R^4$ each independently represents a $C_1$–$C_6$ alkyl group, a $C_2$–$C_6$ alkenyl group, a $C_3$–$C_6$ cycloalkyl group, or a $C_1$–$C_4$ haloalkyl group, or $R^3$ and $R^4$, together with the carbon atom to which they are bonded, form a cycloalkyl group of 5-membered to 7-membered ring, Q represents a cyano group or a group of a formula: —$COR^5$ (wherein $R^5$ represents a hydroxy group, a $C_1$–$C_6$ alkoxy group, an amino group, a $C_1$–$C_6$ alkylamino group, or a $C_1$–$C_6$ dialkylamino group), X represents a halogen atom, a $C_1$–$C_6$ alkyl group, a $C_2$–$C_6$ alkynyl group, a $C_1$–$C_4$ haloalkyl group, a hydroxy group, a $C_1$–$C_6$ alkoxy group, a $C_1$–$C_4$ haloalkoxy group, an aryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a heteroaryloxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylthio group, a $C_1$–$C_4$ haloalkylthio group, a $C_1$–$C_6$ dialkylamino group, a nitro group, a cyano group, or an aryl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), a $C_1$–$C_6$ alkylcarbonyl group, an arylcarbonyl group, or a heteroarylcarbonyl group, Y and Z each independently represents a hydrogen atom, or a halogen atom, and n represents an integer of 0–3, with the exception that $R^3$ and $R^4$ represent a trifluoromethyl group at the same time, and with the proviso that when both $R^1$ and $R^2$ represent a hydrogen atom at the same time, both Y and Z represent a hydrogen atom and n represents an integer of 1–3.

4. A phenylalkane amide derivative represented by Formula (1):

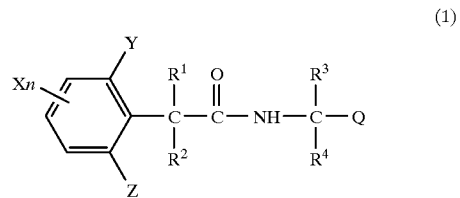

(1)

wherein $R^1$ represents a hydrogen atom, $R^2$ represents a hydrogen atom, or a $C_1$–$C_6$ alkyl group, $R^3$ and $R^4$ each independently represents a $C_1$–$C_6$ alkyl group, a $C_2$–$C_6$ alkenyl group, a $C_3$–$C_6$ cycloalkyl group, or a $C_1$–$C_4$ haloalkyl group, or $R^3$ and $R^4$, together with the carbon atom to which they are bonded, form a cycloalkyl group of 5-membered to 7-membered ring, Q represents a cyano group or a group of a formula: —$COR^5$ (wherein $R^5$ represents a $C_1$–$C_6$ alkoxy group or an amino group), X represents a halogen atom, a $C_1$–$C_6$ alkyl group, a $C_2$–$C_6$ alkynyl group, a $C_1$–$C_4$ haloalkyl group, a $C_1$–$C_6$ alkoxy group, a $C_1$–$C_4$ haloalkoxy group, a phenoxy group (which may be substituted by a $C_1$–$C_6$ alkyl group, a $C_1$–$C_4$ haloalkyl group, a $C_1$–$C_6$ alkoxy group, or a halogen atom), a $C_1$–$C_6$ alkylthio group, a $C_1$–$C_6$ dialkylamino group, a nitro group, a cyano group, a phenyl group (which may be substituted by a $C_1$–$C_6$ alkyl group, a $C_1$–$C_4$ haloalkyl group, a $C_1$–$C_6$ alkoxy group, or a halogen atom), a $C_1$–$C_6$ alkylcarbonyl group, or a benzoyl group, Y and Z represent a hydrogen atom, and n represents an integer of 1–3, with the exception that $R^3$ and $R^4$ represent a trifluoromethyl group at the same time.

5. A phenylalkane amide derivative represented by Formula (1):

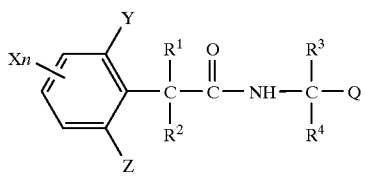 (1)

wherein $R^1$ represents a hydrogen atom, $R^2$ represents a hydrogen atom, or a $C_1$–$C_6$ alkyl group, $R^3$ and $R^4$ each independently represents a $C_1$–$C_6$ alkyl group, a $C_2$–$C_6$ alkenyl group, a $C_3$–$C_6$ cycloalkyl group, or a $C_1$–$C_4$ haloalkyl group, or $R^3$ and $R^4$, together with the carbon atom to which they are bonded, form a cycloalkyl group of 5-membered to 7-membered ring, Q represents a cyano group or a group of a formula: —$COR^5$ (wherein $R^5$ represents a $C_1$–$C_6$ alkoxy group or an amino group), X represents a halogen atom, a $C_1$–$C_6$ alkyl group, a $C_2$–$C_6$ alkynyl group, a $C_1$–$C_4$ haloalkyl group, a $C_1$–$C_6$ alkoxy group, a $C_1$–$C_4$ haloalkoxy group, a phenoxy group, a $C_1$–$C_6$ alkylthio group, a $C_1$–$C_6$ dialkylamino group, a nitro group, or a phenyl group, Y and Z represent a hydrogen atom, and n represents an integer of 1–3, with the exception that $R^3$ and $R^4$ represent a trifluoromethyl group at the same time.

6. An agricultural or horticultural fungicide including a phenylalkane amide derivative as recited in claim 1, as an active ingredient.

7. An agricultural or horticultural fungicide, comprising an effective amount of the phenylalkane amide derivative as recited in claim 1 and a carrier.

8. An agricultural or horticultural fungicide, comprising an effective amount of the phenylalkane amide derivative as recited in claim 2 and a carrier.

9. An agricultural or horticultural fungicide, comprising an effective amount of the phenylalkane amide derivative as recited in claim 3 and a carrier.

10. An agricultural or horticultural fungicide, comprising an effective amount of the phenylalkane amide derivative as recited in claim 4 and a carrier.

11. An agricultural or horticultural fungicide comprising, an effective amount of the phenylalkane amide derivative as recited in claim 5 and a carrier.

12. The phenylalkane amide of claim 1, wherein

Xn is 4-Cl,

Y is H,

Z is H, $R^1$ is methyl, $R^2$ is H, $R^3$ is methyl, $R^4$ is i-Pr, and

Q is CN.

13. The phenylalkane amide of claim 1, wherein

Xn is 4-Cl,

Y is H,

Z is H, $R^1$ is methyl, $R^2$ is H, $R^3$ is methyl, $R^4$ is i-Pr,

Q is $COR^5$, and $R^5$ is methyl.

* * * * *